US010232374B2

United States Patent
Jebrail et al.

(10) Patent No.: US 10,232,374 B2
(45) Date of Patent: Mar. 19, 2019

(54) METHOD OF PROCESSING DRIED SAMPLES USING DIGITAL MICROFLUIDIC DEVICE

(75) Inventors: Mais J. Jebrail, Richmond Hill (CA); Hao Yang, Toronto (CA); Aaron R. Wheeler, Toronto (CA)

(73) Assignee: mirOculus Inc., San Francisco, CA (US)

( * ) Notice: Subject to any disclaimer, the term of this patent is extended or adjusted under 35 U.S.C. 154(b) by 1412 days.

(21) Appl. No.: 13/695,869

(22) PCT Filed: Apr. 15, 2011

(86) PCT No.: PCT/CA2011/050205
§ 371 (c)(1),
(2), (4) Date: Jan. 10, 2013

(87) PCT Pub. No.: WO2011/137533
PCT Pub. Date: Nov. 10, 2011

(65) Prior Publication Data
US 2013/0164856 A1 Jun. 27, 2013

Related U.S. Application Data

(60) Provisional application No. 61/331,679, filed on May 5, 2010.

(51) Int. Cl.
*G01N 1/28* (2006.01)
*B01L 3/00* (2006.01)
(Continued)

(52) U.S. Cl.
CPC ... *B01L 3/502792* (2013.01); *B01L 3/502784* (2013.01); *G01N 1/28* (2013.01);
(Continued)

(58) Field of Classification Search
None
See application file for complete search history.

(56) References Cited

U.S. PATENT DOCUMENTS

| 4,469,863 A | 9/1984 | Ts'o et al. |
| 4,569,575 A | 2/1986 | Le Pesant et al. |

(Continued)

FOREIGN PATENT DOCUMENTS

| CA | 2470847 A1 | 7/2003 |
| CA | 2740113 | 4/2010 |

(Continued)

OTHER PUBLICATIONS

Shih-Kang Fan. Cross-scale electric manipulations of cells and droplets by frequency-modulated dielectrophoresis and electrowetting. The Royal Society of Chemistry (2008), Lab Chip vol. 8, pp. 1325-1331.

(Continued)

*Primary Examiner* — Christopher Adam Hixson
*Assistant Examiner* — Michelle Adams
(74) *Attorney, Agent, or Firm* — Shay Glenn LLP

(57) ABSTRACT

Methods are provided for the preparation of a sample using a digital microfluidic platform and the optional subsequent mass analysis of an extracted analyte. A sample is dried, optionally on a solid phase support, and contacted with digital microfluidic array. An analyte present within the dried sample is extracted into an extraction solvent by electrically addressing the digital microfluidic array to transport a droplet of extraction solvent to the dried sample spot. The extracted sample may be dried and subsequently processed on the digital microfluidic array for derivatization. The digital microfluidic device may further include an integrated microfluidic channel having an output aperture, and the method may further include contacting a droplet (Continued)

containing extracted analyte with the microfluidic channel and applying a suitable electric field for generating nanoelectrospray, thereby enabling the device to be directly interfaced with a mass analysis device.

20 Claims, 10 Drawing Sheets

(51) Int. Cl.
　　*H01J 49/00*　　　(2006.01)
　　*G01N 1/40*　　　(2006.01)
(52) U.S. Cl.
　　CPC . *B01L 3/502753* (2013.01); *B01L 2200/0631* (2013.01); *B01L 2400/0427* (2013.01); *G01N 2001/288* (2013.01); *G01N 2001/4061* (2013.01); *H01J 49/00* (2013.01); *Y10T 436/25* (2015.01)

(56) References Cited

U.S. PATENT DOCUMENTS

| | | |
|---|---|---|
| 4,636,785 A | 1/1987 | Le Pesant |
| 4,818,052 A | 4/1989 | Le Pesant et al. |
| 5,034,506 A | 7/1991 | Summerton et al. |
| 5,130,238 A | 7/1992 | Malek et al. |
| 5,216,141 A | 6/1993 | Benner |
| 5,235,033 A | 8/1993 | Summerton et al. |
| 5,270,185 A | 12/1993 | Margolskee |
| 5,386,023 A | 1/1995 | Sanghvi et al. |
| 5,399,491 A | 3/1995 | Kacian et al. |
| 5,409,818 A | 4/1995 | Davey et al. |
| 5,411,876 A | 5/1995 | Bloch et al. |
| 5,455,166 A | 10/1995 | Walker |
| 5,486,337 A | 1/1996 | Ohkawa |
| 5,602,240 A | 2/1997 | De Mesmaeker et al. |
| 5,637,684 A | 6/1997 | Cook et al. |
| 5,644,048 A | 7/1997 | Yau |
| 5,681,702 A | 10/1997 | Collins et al. |
| 5,705,365 A | 1/1998 | Ryder et al. |
| 5,710,029 A | 1/1998 | Ryder et al. |
| 5,888,779 A | 3/1999 | Kacian et al. |
| 6,007,690 A | 12/1999 | Nelson et al. |
| 6,074,725 A | 6/2000 | Kennedy |
| 6,294,063 B1 | 9/2001 | Becker et al. |
| 6,352,838 B1 | 5/2002 | Krulevitch et al. |
| 6,401,552 B1 | 6/2002 | Elkins |
| 6,565,727 B1 | 5/2003 | Shenderov |
| 6,596,988 B2 | 7/2003 | Corso et al. |
| 6,723,985 B2 | 4/2004 | Schultz et al. |
| 6,773,566 B2 | 8/2004 | Shenderov |
| 6,887,384 B1 | 5/2005 | Frechet et al. |
| 6,911,132 B2 | 6/2005 | Pamula et al. |
| 6,989,234 B2 | 1/2006 | Kolar et al. |
| 7,147,763 B2 | 10/2006 | Elrod et al. |
| 7,163,612 B2 | 1/2007 | Sterling et al. |
| 7,214,302 B1 | 8/2007 | Reihs et al. |
| 7,255,780 B2 | 8/2007 | Shendervo |
| 7,323,345 B1 | 1/2008 | Stjernstrom |
| 7,328,979 B2 | 2/2008 | Decre et al. |
| 7,329,545 B2 | 2/2008 | Pamula et al. |
| 7,349,014 B2 | 3/2008 | Higashihara |
| 7,390,463 B2 | 6/2008 | He et al. |
| 7,391,020 B2 | 6/2008 | Sousse et al. |
| 7,439,014 B2 | 10/2008 | Pamula et al. |
| 7,445,926 B2 | 11/2008 | Mathies et al. |
| 7,531,120 B2 | 5/2009 | Van Rijn et al. |
| D599,832 S | 9/2009 | Chapin et al. |
| 7,713,456 B2 | 5/2010 | Dodd et al. |
| 7,727,723 B2 | 6/2010 | Pollack et al. |
| 7,745,207 B2 | 6/2010 | Jovanovich et al. |
| 7,763,471 B2 | 7/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,901,947 B2 | 3/2011 | Pollack et al. |
| 7,919,330 B2 | 4/2011 | de Guzman et al. |
| 7,998,436 B2 | 8/2011 | Pollack et al. |
| 8,041,463 B2 | 10/2011 | Pollack et al. |
| 8,053,239 B2 | 11/2011 | Wheeler et al. |
| 8,088,578 B2 | 1/2012 | Hua et al. |
| 8,093,062 B2 | 1/2012 | Winger |
| 8,137,917 B2 | 3/2012 | Pollack et al. |
| 8,190,371 B2 | 5/2012 | Atlawi et al. |
| 8,202,686 B2 | 6/2012 | Pamula et al. |
| 8,202,736 B2 | 6/2012 | Mousa et al. |
| 8,208,146 B2 | 6/2012 | Srinivasan et al. |
| 8,268,246 B2 | 9/2012 | Srinivasan et al. |
| 8,304,253 B2 | 11/2012 | Yi et al. |
| 8,317,990 B2 | 11/2012 | Pamula et al. |
| 8,349,276 B2 | 1/2013 | Pamula et al. |
| 8,364,315 B2 | 1/2013 | Sturmer et al. |
| 8,367,370 B2 | 2/2013 | Wheeler et al. |
| 8,389,297 B2 | 3/2013 | Pamula et al. |
| 8,394,641 B2 | 3/2013 | Winger |
| 8,399,222 B2 | 3/2013 | Siva et al. |
| 8,426,213 B2 | 4/2013 | Eckhardt et al. |
| 8,440,392 B2 | 5/2013 | Pamula et al. |
| 8,454,905 B2 | 6/2013 | Pope et al. |
| 8,460,528 B2 | 6/2013 | Pollack et al. |
| 8,470,606 B2 | 6/2013 | Srinivasan et al. |
| 8,481,125 B2 | 7/2013 | Yi et al. |
| 8,492,168 B2 | 7/2013 | Srinivasan et al. |
| 8,562,807 B2 | 10/2013 | Srinivasan et al. |
| 8,591,830 B2 | 11/2013 | Sudarsan et al. |
| 8,592,217 B2 | 11/2013 | Eckhardt |
| 8,613,889 B2 | 12/2013 | Pollack et al. |
| 8,637,317 B2 | 1/2014 | Pamula et al. |
| 8,637,324 B2 | 1/2014 | Pollack et al. |
| 8,658,111 B2 | 2/2014 | Srinivasan et al. |
| 8,685,344 B2 | 4/2014 | Sudarsan et al. |
| 8,685,754 B2 | 4/2014 | Pollack et al. |
| 8,702,938 B2 | 4/2014 | Srinivasan et al. |
| 8,716,015 B2 | 5/2014 | Pollack et al. |
| 8,809,068 B2 | 8/2014 | Sista et al. |
| 8,845,872 B2 | 9/2014 | Pollack et al. |
| 8,846,414 B2 | 9/2014 | Sista et al. |
| 8,852,952 B2 | 10/2014 | Pollack et al. |
| 8,872,527 B2 | 10/2014 | Sturmer et al. |
| 8,877,512 B2 | 11/2014 | Srinivasan et al. |
| 8,888,969 B2 | 11/2014 | Soleymani et al. |
| 8,926,065 B2 | 1/2015 | Winger |
| 8,927,296 B2 | 1/2015 | Sista et al. |
| 8,936,708 B2 | 1/2015 | Feiglin et al. |
| 8,951,732 B2 | 2/2015 | Pollack et al. |
| 8,980,198 B2 | 3/2015 | Srinivasan et al. |
| 9,005,544 B2 | 4/2015 | Van Dam et al. |
| 9,011,662 B2 | 4/2015 | Wang et al. |
| 9,046,514 B2 | 6/2015 | Sista et al. |
| 9,091,649 B2 | 7/2015 | Pollack et al. |
| 9,248,450 B2 | 2/2016 | Bauer |
| 9,476,811 B2 | 10/2016 | Mudrik et al. |
| 9,476,856 B2 | 10/2016 | Pamula et al. |
| 9,517,469 B2 | 12/2016 | Shenderov et al. |
| 9,594,056 B2 | 3/2017 | Fobel et al. |
| 2002/0150683 A1 | 10/2002 | Troian et al. |
| 2003/0017551 A1 | 1/2003 | Parthasarathy et al. |
| 2003/0136451 A1 | 7/2003 | Beebe et al. |
| 2003/0194716 A1 | 10/2003 | Knoll |
| 2004/0171169 A1 | 9/2004 | Kallury et al. |
| 2004/0211659 A1 | 10/2004 | Velev |
| 2005/0115836 A1 | 6/2005 | Reihs |
| 2005/0133370 A1 | 6/2005 | Park et al. |
| 2005/0148091 A1 | 7/2005 | Kitaguchi et al. |
| 2005/0191759 A1 | 9/2005 | Pedersen-Bjergaard et al. |
| 2005/0220675 A1 | 10/2005 | Reed et al. |
| 2006/0091015 A1 | 5/2006 | Lau |
| 2006/0132542 A1 | 6/2006 | Bruker et al. |
| 2006/0231398 A1 | 10/2006 | Sarrut et al. |
| 2006/0272942 A1 | 12/2006 | Sirringhaus |
| 2007/0023292 A1 | 2/2007 | Kim et al. |
| 2007/0095407 A1 | 5/2007 | Chen et al. |
| 2007/0148763 A1 | 6/2007 | Huh et al. |

(56) References Cited

U.S. PATENT DOCUMENTS

| | | |
|---|---|---|
| 2007/0242111 A1 | 10/2007 | Pamula et al. |
| 2007/0269825 A1 | 11/2007 | Wang et al. |
| 2008/0044914 A1 | 2/2008 | Pamula et al. |
| 2008/0110753 A1 | 5/2008 | Fourrier et al. |
| 2008/0131904 A1 | 6/2008 | Parce et al. |
| 2008/0156983 A1 | 7/2008 | Fourrier et al. |
| 2008/0169197 A1 | 7/2008 | McRuer et al. |
| 2008/0185339 A1 | 8/2008 | Delapierre et al. |
| 2008/0210558 A1 | 9/2008 | Sauter-Starace et al. |
| 2008/0241831 A1 | 10/2008 | Fan et al. |
| 2008/0281471 A1 | 11/2008 | Smith |
| 2008/0293051 A1 | 11/2008 | Levy et al. |
| 2009/0017197 A1 | 1/2009 | Zhang et al. |
| 2009/0017453 A1 | 1/2009 | Maples et al. |
| 2009/0203063 A1 | 8/2009 | Wheeler et al. |
| 2010/0025250 A1 | 2/2010 | Pamula et al. |
| 2010/0032293 A1 | 2/2010 | Pollack et al. |
| 2010/0041086 A1* | 2/2010 | Pamula .......... B01L 3/502784 435/18 |
| 2010/0048410 A1 | 2/2010 | Shenderov et al. |
| 2010/0081578 A1 | 4/2010 | Wheeler et al. |
| 2010/0087012 A1 | 4/2010 | Shenderov |
| 2010/0087633 A1 | 4/2010 | Wheeler et al. |
| 2010/0120130 A1 | 5/2010 | Srinivasan et al. |
| 2010/0130369 A1 | 5/2010 | Shenderov et al. |
| 2010/0136544 A1 | 6/2010 | Agresti et al. |
| 2010/0206094 A1 | 8/2010 | Shenderov |
| 2010/0213074 A1 | 8/2010 | Mousa et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0270156 A1 | 10/2010 | Srinivasan et al. |
| 2010/0311599 A1 | 10/2010 | Wheeler et al. |
| 2011/0024793 A1 | 2/2011 | Jeon |
| 2011/0076685 A1 | 3/2011 | Moeller et al. |
| 2011/0097763 A1 | 4/2011 | Pollack et al. |
| 2011/0104725 A1 | 5/2011 | Pamula et al. |
| 2011/0104747 A1 | 5/2011 | Pollack et al. |
| 2011/0107822 A1 | 5/2011 | Bunner et al. |
| 2011/0147216 A1 | 6/2011 | Fan et al. |
| 2011/0240471 A1 | 10/2011 | Wheeler et al. |
| 2011/0247934 A1 | 10/2011 | Wang et al. |
| 2011/0293851 A1 | 12/2011 | Bollström et al. |
| 2011/0303542 A1 | 12/2011 | Srinivasan et al. |
| 2011/0311980 A1 | 12/2011 | Pollack et al. |
| 2012/0045748 A1 | 2/2012 | Willson et al. |
| 2012/0045768 A1 | 2/2012 | Arunachalam et al. |
| 2012/0083046 A1 | 4/2012 | Watson et al. |
| 2012/0085645 A1 | 4/2012 | Mousa et al. |
| 2012/0136147 A1* | 5/2012 | Winger .................... C12Q 1/25 536/123.1 |
| 2012/0149018 A1 | 6/2012 | Dahlberg et al. |
| 2012/0190027 A1 | 7/2012 | Loeffert et al. |
| 2012/0259233 A1 | 10/2012 | Chan et al. |
| 2012/0261264 A1 | 10/2012 | Srinivasan et al. |
| 2012/0325665 A1 | 12/2012 | Chiou et al. |
| 2013/0105318 A1 | 5/2013 | Bhattacharya et al. |
| 2013/0168250 A1 | 7/2013 | Fogleman et al. |
| 2013/0177915 A1 | 7/2013 | Too et al. |
| 2013/0203606 A1 | 8/2013 | Pollack et al. |
| 2013/0215492 A1 | 8/2013 | Steckl et al. |
| 2013/0217113 A1 | 8/2013 | Srinivasan et al. |
| 2013/0225450 A1 | 8/2013 | Pollack et al. |
| 2013/0284956 A1 | 10/2013 | Kwon |
| 2013/0288254 A1 | 10/2013 | Pollack et al. |
| 2013/0293246 A1 | 11/2013 | Pollack et al. |
| 2013/0306480 A1 | 11/2013 | Chang et al. |
| 2014/0141409 A1 | 5/2014 | Foley et al. |
| 2015/0001078 A1 | 1/2015 | Feiglin |
| 2016/0319354 A1 | 11/2016 | Tocigl et al. |
| 2016/0370317 A9 | 12/2016 | Sudarsan et al. |
| 2017/0315090 A1 | 11/2017 | Wheeler et al. |
| 2018/0120335 A1 | 5/2018 | Mousa et al. |

FOREIGN PATENT DOCUMENTS

| | | |
|---|---|---|
| CN | 101609063 A | 12/2009 |
| CN | 102549804 A | 7/2012 |
| EP | 2111554 B1 | 5/2013 |
| JP | 2002321449 A | 11/2002 |
| JP | 2006220606 A | 8/2006 |
| JP | 2010098133 A | 4/2010 |
| JP | 2010515877 A | 5/2010 |
| JP | 2010180222 A | 8/2010 |
| JP | 2012525687 A | 10/2012 |
| WO | WO2000/067907 A2 | 11/2000 |
| WO | WO2001/025137 A1 | 4/2001 |
| WO | WO2003/045556 A2 | 6/2003 |
| WO | WO2004/074169 A1 | 9/2004 |
| WO | WO2005/068993 A1 | 7/2005 |
| WO | WO2005/118129 A1 | 12/2005 |
| WO | WO2006/000828 A2 | 1/2006 |
| WO | WO2006/102309 A2 | 9/2006 |
| WO | 2007120241 | 10/2007 |
| WO | WO2007/120240 A2 | 10/2007 |
| WO | 2007130294 A2 | 11/2007 |
| WO | 2007136386 | 11/2007 |
| WO | WO2007/123908 A2 | 11/2007 |
| WO | 2008051310 | 5/2008 |
| WO | 2008066828 A2 | 6/2008 |
| WO | WO2009/026339 A2 | 2/2009 |
| WO | WO2009/052348 A2 | 4/2009 |
| WO | WO 2009/111431 A2 * | 9/2009 |
| WO | WO2009/111723 A1 | 9/2009 |
| WO | WO2009/111769 A2 | 9/2009 |
| WO | WO2009/140671 A2 | 11/2009 |
| WO | WO2010/003188 A1 | 1/2010 |
| WO | WO2010/006166 A2 | 1/2010 |
| WO | WO2010/027894 A2 | 3/2010 |
| WO | 2010040227 | 4/2010 |
| WO | WO2010/042637 A2 | 4/2010 |
| WO | WO2010/069977 A1 | 6/2010 |
| WO | WO2010/091334 A2 | 8/2010 |
| WO | 2010111265 A1 | 9/2010 |
| WO | WO2011/002957 A2 | 1/2011 |
| WO | WO2011/062557 A1 | 5/2011 |
| WO | WO2016/197103 A1 | 12/2016 |
| WO | WO2016/197106 A1 | 12/2016 |

OTHER PUBLICATIONS

Ting-Hsuan Chen. Selective Wettability Assisted Nanoliter Sample Generation via Electrowetting-Based Transportation. Proceedings of the Fifth International Conference on Nanochannels, Microchannels and Minichannels (ICNMM) (Jun. 18-20, 2007).

Hongmei Yu. A plate reader-compatible microchannel array for cell biology assays. The Royal Society of Chemistry (2007) Lab Chip vol. 7, pp. 388-391.

Marc A. Unger. Monolithic Microfabricated Valves and Pumps by Multilayer Soft Lithography. Science (2000) vol. 288.

A.S. Verkman. Drug Discovery in Academia. Am J Physiol Cell Physiol (2004) vol. 286, pp. 465-474.

Jamil El-Ali. Cells on chips. Nature (2006) Insight Review. vol. 442.

Darren R. Link. Electric Control of Droplets in Microfluidic Devices. Communications. Angew Chem. Int (2006) vol. 45 pp. 2556-2560.

Wheeler Aaron A. Electrowetting-Based Microfluidics for Analysis of Peptides and Proteins by Matrix-Assisted Laser Desorption/Ionization Mass Spectrometry. (Aug. 2004) Anal Chem. vol. 76, No. 16.

Eun Zoo Lee. Removal of bovine serum albumin using solid-phase extraction with in-situ polymerized stationary phase in a microfluidic device. ScienceDirect. Journal of Chromatography A. (2008) vol. 1187. pp. 11-17.

Hsih Yin Tan. A lab-on-a-chip for detection of nerve agent sarin in blood. The Royal Society of Chemistry (2008). Lab Chip vol. 8. pp. 885-891.

Kai-Cheng Chuang. Direct Handwriting Manipulation of Droplets by Self-Aligned Mirror-EWOD Across a Dielectric Sheet. MEMS (Jan. 2006) pp. 22-26.

(56) References Cited

OTHER PUBLICATIONS

Mohamed Abdelgawad. Low-cost, rapid-prototyping of digital microfluidics devices. Springer. Microfluid Nanofluid (2008) vol. 4. pp. 349-355.
Eric Lebrasseur. Two-dimensional electrostatic actuation of droplets using a single electrode panel and development of disposable plastic film card. ScienceDirect. Sensors and Actuators (2007) vol. 136. pp. 358-366.
Chatterjee et al. Droplet-based microfluidics with nonaqueous solvents and solutions. Lap Chip. 2006. vol. 6. pp. 199-206.
Jebrail et al. Digital Microfluidic Method for Protein Extraction by Precipitation. Analytical Chemistry. Jan. 1, 2009. vol. 81. No. 1. pp. 330-335.
Moon et al., "An integrated digital microfluidic chip for multiplexed proteomic sample preparation and analysis by MALDI-MS", Lab Chip, 2006, vol. 6, pp. 1213-1219.
Kutter, J. P.; Jacobson, S. C.; Matsubara, N.; Ramsey, J. M. "Solvent-Programmed Microchip Open-Channel Electrochromatography", Analytical Chemistry 1998, 70, 3291-3297.
Kutter, J. P.; Jacobson, S. C.; Ramsey, J. M. "Solid phase extraction on microfluidic devices", Journal of Microcolumn Separations 2000, 12, 93-97.
Bergkvist, J.; Ekstrom, S.; Wallman, L.; Lofgren, M.; Marko-Varga, G.; Nilsson, J.; Laurell, T. "Improved chip design for integrated solid-phase microextraction in on-line proteomic sample preparation", Proteomics 2002, 2, 422-429.
Ekstrom, S.; Malmstrom, J.; Wallman, L.; Lofgren, M.; Nilsson, J.; Laurell, T.; Marko-Varga, G. "On-chip microextraction for proteomic sample preparation of in-gel digests", Proteomics 2002, 2, 413-421.
Ekstrom, S.; Wallman, L.; Hok, D.; Marko-Varga, G.; Laurell, T. "Miniaturized solid-phase extraction and sample preparation for MALDI MS using a microfabricated integrated selective enrichment target", Journal of Proteome Research 2006, 5, 1071-1081.
Ekstrom, S.; Wallman, L.; Helldin, G.; Nilsson, J.; Marko-Varga, G.; Laurell, T. "Polymeric integrated selective enrichment target (ISET) for solid-phase-based sample preparation in MALDI-TOF MS", Journal of Mass Spectrometry 2007, 42, 1445-1452.
Jemere, A. B.; Oleschuk, R. D.; Ouchen, F.; Fajuyigbe, F.; Harrison, D. J. "An integrated solid-phase extraction system for sub-picomolar detection", Electrophoresis 2002, 23, 3537-3544.
Li, J.; LeRiche, T.; Tremblay, T. L.; Wang, C.; Bonneil, E.; Harrison, D. J.; Thibault, P. "Application of microfluidic devices to proteomics research: identification of trace-level protein digests and affinity capture of target peptides", Molecular & cellular proteomics : MCP 2002, 1, 157-168.
Oleschuk, R. D.; Shultz-Lockyear, L. L.; Ning, Y.; Harrison, D. J. "Trapping of bead-based reagents within microfluidic systems: On-chip solid-phase extraction and electrochromatography", Analytical Chemistry 2000, 72, 585-590.
Lettieri, G. L.; Dodge, A.; Boer, G.; De Rooij, N. F.; Verpoorte, E. "A novel microfluidic concept for bioanalysis using freely moving beads trapped in recirculating flows", Lab on a Chip—Miniaturisation for Chemistry and Biology 2003, 3, 34-39.
Foote, R. S.; Khandurina, J.; Jacobson, S. C.; Ramsey, J. M. "Preconcentration of proteins on microfluidic devices using porous silica membranes", Analytical Chemistry 2005, 77, 57-63.
Hatch, A. V.; Herr, A. E.; Throckmorton, D. J.; Brennan, J. S.; Singh, A. K. "Integrated preconcentration SDS-PAGE of proteins in microchips using photopatterned cross-linked polyacrylamide gels", Analytical Chemistry 2006, 78, 4976-4984.
Petersen, N. J.; Jensen, H.; Hansen, S. H.; Foss, S. T.; Snakenborg, D.; Pedersen-Bjergaard, S. "On-chip electro membrane extraction", Microfluidics and Nanofluidics 2010, 1-8.
Bonneil, E.; Li, J.; Tremblay, T. L.; Bergeron, J. J.; Thibault, P. "Integration of solid-phase extraction membranes for sample multiplexing: Application to rapid protein identification from gel-isolated protein extracts", Electrophoresis 2002, 23, 3589-3598.
Yu, C.; Davey, M. H.; Svec, F.; Frechet, J. M. J. "Monolithic porous polymer for on-chip solid-phase extraction and preconcentration prepared by photoinitiated in situ polymerization within a microfluidic device", Analytical Chemistry 2001, 73, 5088-5096.
Yu, C.; Xu, M.; Svec, F.; Frechet, J. M. J. "Preparation of monolithic polymers with controlled porous properties for microfluidic chip applications using photoinitiated free-radical polymerization", Journal of Polymer Science, Part A: Polymer Chemistry 2002, 40, 755-769.
Lee, J.; Moon, H.; Fowler, J.; Schoellhammer, T.; Kim, C. J. "Electrowetting and electrowetting-on-dielectric for microscale liquid handling", Sensors and Actuators, A: Physical 2002, 95, 259-268.
Pollack, M. G.; Fair, R. B.; Shenderov, A. D. "Electrowetting-based actuation of liquid droplets for microfluidic applications", Applied Physics Letters 2000, 77, 1725-1726.
Wheeler, A. R. "Chemistry: Putting electrowetting to work", Science 2008, 322, 539-540.
Abdelgawad, M.; Freire, S. L. S.; Yang, H.; Wheeler, A. R. "All-terrain droplet actuation", Lab on a Chip—Miniaturisation for Chemistry and Biology 2008, 8, 672-677.
Jebrail, M. J.; Wheeler, A. R. "Digital microfluidic method for protein extraction by precipitation", Analytical Chemistry 2009, 81, 330-335.
Mousa, N. A. J., M.J.; Yang, H.; Abdegawad, M.; Metalnikov, P.; Chen, J.; Wheeler, A.R.; Casper, R.F. "Droplet-Scale Estrogen Assays in Breast Tissue, Blood, and Serum", Sci. Trans. Med. 2009, 1, 1ra2.
Jebrail, M.J.; Luk, V. N.; Shih, S.C.C.; Fobel, R.; Ng, A.H.C.; Yang, H.; Freire, S.L.S.; Wheeler, A.R. Journal of Visualized Experiments. 2009, 33, DOI: 10.3791/1603.
Millington, D.S., et al., Digital Microfluidics: A Novel Platform for Multiplexed Detection of LSDs with Potential for Newborn Screening, Oak Ridge Conference (2009).
Millington, D.S., et al., Digital Microfluidics: A Future Technology in the Newborn Screening Laboratory?, Sem. In Perinat. 34 (2), 163-169 (2010).
Abdelgawad et al.; Rapid prototyping in copper substrates for digital microfluidics, Adv. Mater., 19(1), pp. 133-137; Jan. 2007.
Abdelgawad et al; Hybrid microfluidics: a digital-to-channel interface for in-line sample processing and chemical separations, Lab on a Chip, 9(8), pp. 1046-1051, Apr. 2009.
Abdelgawad; Digital Microfluidics for Integration of Lab-on-a-Chip Devices (Doctoral dissertation); University of Toronto; © 2009.
Albrecht et al.; Laboratory testing of gonadal steroids in children; Pediatric Endocrinology Reviews; 5(suppl 1); pp. 599-607; Oct. 2007.
Ankarberg-Lindren et al.; A purification step prior to commercial sensitive immunoassay is necessary to achieve clinical usefulness when quantifying serum 17 ?-estradiol in prepubertal children. Eur J Endocrinol, 158, pp. 117-124, Jan. 2008.
Armstrong et al.; A study of plasma free amino acid levels. II. Normal values for children and adults, Metabolism, 22(4), pp. 561-569, Apr. 1973.
Asiello et al.; Miniaturized isothermal nucleic acid amplification, a review; Lab Chip; 11(8); pp. 1420-1430; Apr. 2011.
Au et al., Integrated microbioreactor for culture and analysis of bacteria, algae and yeast, Biomedical Microdevices, 13(1), pp. 41-50, Feb. 2011.
Banatvala et al., Rubella, The Lancet, 363(9415), pp. 1127-1137, Apr. 2004.
Banér et al.; Signal amplification of padlock probes by rolling circle replication; Nuc. Acids Res.; 26(22); pp. 5073-5078; Nov. 1998.
Barany; Genetic disease detection and DNA amplification using cloned thermostable ligase; PNAS; 88(1); pp. 189-193; Jan. 1991.
Barbulovic-Nad et al., A microfluidic platform for complete mammalian cell culture, Lab on a Chip, 10(12), pp. 1536-1542; Jun. 2010.
Barbulovic-Nad et al.; Digital microfluidics for cell-based assays, Lab Chip, 8(4), pp. 519-526; Apr. 2008.
Beattie et al.; Endogenous sex hormones, breast cancer risk, and tamoxifen response: an ancillary study in the NSABP Breast Cancer Prevention Trial P-1, J Natl Cancer Inst, 98(2), pp. 110-115, Jan. 2006.

(56) References Cited

OTHER PUBLICATIONS

Beaucage et al., The Functionalization of Oligonucleotides via Phosphoramidite Derivatives,Tetrahedron, 49(10), pp. 1925-1963, Mar. 1993.
Belanger et al.; Omental and subcutaneous adipose tissue steroid levels in obese men. Steroids, 71(8), pp. 674-682, Aug. 2006.
Blankenstein et al.; Intratumoral levels of estrogens in breast cancer. J Steroid Biochem Mol Biol, 69(1-6), pp. 293-297, Apr.-Jun. 1999.
Bodamer et al.; Expanded newborn screening in Europe, Journal of Inherited Metabolic Disease, 30(4), pp. 439-444, Aug. 2007.
Bohlen et al.; Fluorometric assay of proteins in the nanogram range, Archives of Biochemistry and Biophysics, 155(1), pp. 213-220, Mar. 1973.
Bollström et al.; A Multilayer Coated Fiber-Based Substrate Suitable for Printed Functionality; Organic Electronics; 10(5); pp. 1020-1023; Aug. 2009.
Brassard et al.; Water-oil core-shell droplets for electrowetting-based digital microfluidic devices; Lab Chip; 8(8); pp. 1342-1349; Aug. 2008.
Brill et al., Synthesis of oligodeoxynucleoside phosphorodithioates via thioamidites, J. Am. Chem. Soc., 111(6), pp. 2321-2322, Mar. 1989.
Brivio et al.; Integrated microfluidic system enabling (bio)chemical reactions with on-line MALDI-TOF mass spectrometry, Anal. Chem., 74(16), pp. 3972-3976, Aug. 2002.
Burstein; Aromatase inhibitor-associated arthralgia syndrome. Breast, 16(3), pp. 223-234, Jun. 2007.
Carlsson et al., Screening for genetic mutations, Nature, 380(6571), pp. 207, Mar. 1996.
Chace et al.; A biochemical perspective on the use of tandem mass spectrometry for newborn screening and clinical testing, Clinical Biochemistry, 38(4), pp. 296-309; Apr. 2005.
Chace et al.; Rapid diagnosis of maple syrup urine disease in blood spots from newborns by tandem mass spectrometry, Clinical Chemistry, 41(1), pp. 62-68, Jan. 1995.
Chace et al.; Rapid diagnosis of phenylketonuria by quantitative analysis for phenylalanine and tyrosine in neonatal blood spots by tandem mass spectrometry, Clinical Chemistry, 39(1), pp. 66-71; Jan. 1993.
Chace et al.; Use of tandem mass spectrometry for multianalyte screening of dried blood specimens from newborns, Clinical Chemistry, 49(11), pp. 1797-1817, Nov. 2003.
Chace; Mass spectrometry in newborn and metabolic screening: historical perspective and future directions, Journal of Mass Spectrometry, 44(2), pp. 163-170, Feb. 2009.
Chang et al.; Integrated polymerase chain reaction chips utilizing digital microfluidics; Biomedical Microdevices; 8(3); pp. 215-225; Sep. 2006.
Cheng et al., Paper-Based ELISA, Angewandte Chemie, 49(28), pp. 4771-4774, Jun. 2010.
Cheng et al.; Highly Sensitive Determination of microRNA Using Target-Primed and Branched Rolling-Circle Amplification; Angew. Chem.; 121(18); pp. 3318-3322; Apr. 2009.
Chetrite et al.; Estradiol inhibits the estrone sulfatase activity in normal and cancerous human breast tissues. Journal of Steroid Biochemistry and Molecular Biology, 104(3-5), pp. 289-292, May 2007.
Cho et al.; Creating, transporting, cutting, and merging liquid droplets by electrowetting-based actuation for digital microfluidic circuits, J. MEMS 2003, 12(1), pp. 70-80, Feb. 2003.
Christiansen; Hormone Replacement Therapy and Osteoporosis; Maturitas, 23, Suppl. pp. S71-S76, May 1996.
Cipriano et al.; The cost-effectiveness of expanding newborn screening for up to 21 inherited metabolic disorders using tandem mass spectrometry: results from a decision-analytic model, Value in Health, 10(2), pp. 83-97, Mar.-Apr. 2007.
Cooney et al.; Electrowetting droplet microfluidics on a single planar surface, Microfluid. Nanofluid., 2(5), pp. 435-446; Sep. 2006.

Crabtree et al.; Microchip injection and separation anomalies due to pressure effects, Anal. Chem., 73(17), pp. 4079-4086, Sep. 2001.
Cunningham; Testosterone replacement therapy for late-onset hypogonadism. Nature Clinical Practice Urology, 3(5), pp. 260-267, May 2006.
Cuzick; Chemoprevention of breast cancer. Women's Health, 2(6), pp. 853-861, Nov. 2006.
Dahlin et al.; Poly(dimethylsiloxane)-based microchip for two-dimensional solid-phase extraction-capillary electrophoresis with an integrated electrospray emitter tip, Anal. Chem., 77(16), pp. 5356-5363, Aug. 2005.
Danton et al.; Porphyrin profiles in blood, urine and faeces by HPLC/electrospray ionization tandem mass spectrometry. Biomedical Chromatography, 20(6-7), pp. 612-621, Jun.-Jul. 2006.
De Mesmaeker et al.; Comparison of rigid and flexible backbones in antisense oligonucleotides; Bioorganic & Medicinal Chem. Lett; 4(3); pp. 395-398; Feb. 1994.
Deligeorgiev et al.; Intercalating Cyanine Dyes for Nucleic Acid Detection; Recent Pat Mat Sci; 2(1); pp. 1-26; Jan. 2006.
Dempcy et al., Synthesis of a thymidyl pentamer of deoxyribonucleic guanidine and binding studies with Dna homopolynucleotides, Proc. Natl. Acad. Sci., 92(13), pp. 6097-6101, Jun. 1995.
Deng et al.; Rapid determination of amino acids in neonatal blood samples based on derivatization with isobutyl chloroformate followed by solid-phase microextraction and gas chromatography/mass spectrometry. Rapid Communications in Mass Spectrometry, 18(1), pp. 2558-2564, Nov. 2004.
Dibbelt et al.; Determination of natural and synthetic estrogens by radioimmunoassay: Comparison of direct and extraction methods for quantification of estrone in human serum. Clinical Laboratory, 44(3), 137-143, Mar. 1998.
Dietzen et al.; National academy of clinical biochemistry laboratory medicine practice guidelines: follow-up testing for metabolic disease identified by expanded newborn screening using tandem spectrometry; executive summary, Clinical Chemistry, 55(9), pp. 1615-1626, Sep. 2009.
Diver et al.; Warning on plasma oestradiol measurement. Lancet, 330(8567), p. 1097, Nov. 1987.
Divino Filho et al.; Simultaneous measurements of free amino acid patterns of plasma, muscle and erythrocytes in healthy human subjects, Clinical Nutrition, 16(6), pp. 299-305, Dec. 1997.
Djerassi; Chemical birth of the pill. American Journal of Obstetrics and Gynecology, 194(1), pp. 290-298, Jan. 2006.
Dobrowolski et al.; DNA microarray technology for neonatal screening, Acta Paediatrica Suppl, 88(432), pp. 61-64, Dec. 1999.
Duffy et al.; Rapid prototyping of microfluidic systems in Poly (dimethylsiloxane), Anal. Chem., 70(23), pp. 4974-4984, Dec. 1998.
Edgar et al.; Capillary electrophoresis separation in the presence of an immiscible boundary for droplet analysis, Anal. Chem., 78(19), pp. 6948-6954 (author manuscript, 15 pgs.), Oct. 2006.
Egholm et al., PNA hybridizes to complementary oligonucleotides obeying the Watson-Crick hydrogen-bonding rules, Nature, 365(6446), pp. 566-568, Oct. 1993.
Egholm et al., Recognition of guanine and adenine in DNA by cytosine and thymine containing peptide nucleic acids (PNA), J. Am. Chem. Soc., 114(24), pp. 9677-9678; Nov. 1992.
Ehrmann; Polycystic ovary syndrome. New England Journal of Medicine; 352(12); pp. 1223-1236; Mar. 2005.
El-Ali et al.; Cells on chips; Nature (2006) insight Review; 442(7101); pp. 403-411; Jul. 2006.
Fair; Digital microfluidics: Is a true lab-on-a-chip possible?; Microfuid. Nanofluid.; 3(3); pp. 245-281; Jun. 2007.
Falk et al.; Measurement of Sex Steroid Hormones in Breast Adipocytes: Methods and Implications; Cancer Epidemiol Biomarkers Prev; 17(8); pp. 1891-1895; Aug. 2008.
Fan et al.; Electrically Programmable Surfaces for Configurable Patterning of Cells; Advanced Materials; 20(8); pp. 1418-1423; Apr. 2008.
Freire et al.; A practical interface for microfluidics and nanoelectrospray mass spectrometry, Electrophoresis, 29(9), pp. 1836-1843, May 2008.

(56) References Cited

OTHER PUBLICATIONS

Fu et al., Controlled Reagent Transport in Disposable 2D Paper Networks, Lab. Chip, 10(7), pp. 918-920 (author manuscript, 9 pgs.), Apr. 2010.
Gao et al.; Unusual conformation of a 3'-thioformacetal linkage in a DNA duplex; J. Biomol. NMR; 4(1); pp. 17-34; Jan. 1994.
Gentili et al.; Analysis of free estrogens and their conjugates in sewage and river waters by solid-phase extraction then liquid chromatography-electrospray-tandem mass spectrometry. Chromatographia 56(1), pp. 25-32, Jul. 2002.
Gerasimova et al.; Fluorometric method for phenylalanine microplate assay adapted for phenylketonuria screening, Clinical Chemistry, 35(10), pp. 2112-2115, Oct. 1989.
Gong et al., All-Electronic Droplet Generation On-Chip With Real-Time Feedback Control for Ewod Digital Microfluidics, Lab Chip, 8(6), pp. 898-906 (author manuscript, 20 pgs.), Jun. 2008.
Gong et al.; Portable digital microfluidics platform with active but disposable lab-on-chip; 17th IEEE International Conference on Micro Electro Mechanical Systems; Maastricht, Netherlands; pp. 355-358; Jan. 24-29, 2004.
Gong et al.; Two-dimensional digital microfluidic system by multilayer printed circuit board, 18th IEEE International Conference on Micro Electro Mechanical Systems (MEMS 2005); IEEE; pp. 726-729; Jan. 30-Feb. 3, 2005.
Goto et al.; Colorimetric detection of loop-mediated isothermal amplification reaction by using hydroxy naphthol blue; Biotechniques; 46(3); pp. 167-172; Mar. 2009.
Gottschlich et al.; Integrated microchip-device for the digestion, separation and postcolumn labeling of proteins and peptides, J. Chromatogr. B, 745(1), pp. 243-249, Aug. 2000.
Green et al.; Neonatal screening by DNA microarray: spots and chips, Nature Reviews Genetics, 6(2), pp. 147-151, Feb. 2005.
Henderson et al.; Estrogens as a cause of human cancer: The Richard and Hinda Rosenthal Foundation award lecture. Cancer Res, 48(2), pp. 246-253, Jan. 1988.
Herdewijn et al.; 2'-5'-Oligoadenyiates (2-5A) as Mediators of Interferon Action. Synthesis and Biological Activity of New 2-5A Analogues. E. De Clerq (ed.) Frontiers in Microbiology, 231-232, Springer, Dordrecht Jan. 1987.
Hertz et al.; Estrogen-progestogen combinations for contraception. Journal of the American Medical Association, 198(9), pp. 1000-1006, Nov. 1966.
Horn et al.; Oligonucleotides with alternating anionic and cationic phosphoramidate linkages: Synthesis and hybridization of stereouniform isomers; Tetrahedron Lett.; 37(6); pp. 743-746; Feb. 1996.
Huh et al.; Reversible Switching of High-Speed Air-Liquid Two-Phase Flows Using Electrowetting-Assisted Flow-Pattern Change, J. Am. Chem. Soc., 125, pp. 14678-14679; Dec. 2003.
Jacobson et al.; High-Speed Separations on a Microchip, Anal. Chem., 66(7), pp. 1114-1118, Apr. 1994.
Jacobson et al.; Precolumn Reactions with Electrophoretic Analysis Integrated on a Microchip, Anal. Chem., 66(23), pp. 4127-4132, Dec. 1994.
Jebrail et al.; Let's get digital: digitizing chemical biology with microfluidics, Curr. Opin. Chem. Biol., 14(5), 574-581, Oct. 2010.
Jebrail et al., Synchronized synthesis of peptide-based macrocycles by digital microfluidics, Angew. Chem. Int. Ed. Eng., 49(46), pp. 8625-8629, Nov. 2010.
Jenkins et al., The biosynthesis of carbocyclic nucleosides; Chem. Soc. Rev.; 24(3); pp. 169-176; Jan. 1995.
Jessome et al.; Ion Suppression: A Major Concern in Mass Spectrometry. LC-GC North America, 24(5), pp. 498-510, May 2006.
Jia et al.; Ultrasensitive detection of microRNAs by exponential isothermal amplification; Angew. Chem. Int. Ed. Engl.; 49(32); pp. 5498-5501; Jul. 2010.
Jung et al.; Hybridization of Alternating Cationic/Anionic Oligonucleotides to RNA Segments; Nucleosides & Nucleotides; 13(6-7); pp. 1597-1605; Jul. 1994.

Kaaks et al.; Postmenopausal serum androgens, oestrogens and breast cancer risk: The European prospective investigation into cancer and nutrition. Endocrine-Related Cancer,12(4), pp. 1071-1082, Dec. 2005.
Kiedrowski et al., Parabolic Growth of a Self-Replicating Hexadeoxynucleotide Bearing a 3'-5'-Phosphoamidate Linkage; Angew. Chemie Intl. Ed.; 30(4); pp. 423-426; Apr. 1991.
Kim et al.; Microfabricated Monolithic Multinozzle Emitters for Nanoelectrospray Mass Spectrometry; Anal Chem; 79(10); pp. 3703-3707; May 2007.
Kralj et al.; Integrated continuous microfluidic liquid-liquid extraction. Lab on a Chip, 7(2), pp. 256-263, Feb. 2007.
Labrie et al.; Androgen glucuronides, instead of testosterone, as the new markers of androgenic activity in women. The Journal of Steroid Biochemistry and Molecular Biology, 99(4-5), pp. 182-188, Jun. 2006.
Labrie; Intracrinology. Molecular and Cellular Endocrinology, 78(3), pp. C113-C118, Jul. 1991.
Lamar et al.; Serum sex hormones and breast cancer risk factors in postmenopausal women. Cancer Epidemiol Biomarkers Prey, 12(4), pp. 380-383, Apr. 2003.
Lawyer et al.; High-level expression, purification, and enzymatic characterization of full-length Thermos aquaticus DNA polymerase and a truncated form deficient in 5' to 3' exonuclease activity; Genome Res; 2(41; pp. 275-287; May 1993.
Lawyer et al.; Isolation, characterization, and expression in *Escherichia coli* of the DNA polymerase gene from Thermus aquaticus; J. Biol. Chem.; 264; pp. 6427-6437; Apr. 1989.
Lee et al.; Surface-Tension-Driven Microactuation Based on Continuous Electrowetting; J. Microelectromechanical Systems; 9(2); pp. 171-180; Jun. 2000.
Letsinger et al., Cationic oligonucleotides, J. Am. Chem. Soc., 110(13), pp. 4470-4471, Jun. 1988.
Letsinger et al., Effects of pendant groups at phosphorus on binding properties of d-ApA analogues, Nucl. Acids Res., 14(8), pp. 3487-3499, Apr. 1986.
Letsinger et al., Phosphoramidate analogs of oligonucleotides, J. Org. Chem., 35(11), pp. 3800-3803, Nov. 1970.
Levy et al.; Genetic screening of newborns, Annual Review of Genomics and Human Genetics, 1, pp. 139-177, Sep. 2000.
Li et al., Paper-based microfluidic devices by plasma treatment, Anal. Chem., 80(23), pp. 9131-9134, Nov. 2008.
Li et al.; One-step ultrasensitive detection of microRNAs with loop-mediated isothermal amplification (LAMP); Chem Commun; 47(9); pp. 2595-2597; Mar. 2011.
Link et al.; Electric Control of Droplets in Microfluidic Devices; Angew Chem Int Ed Engl; 45(16); pp. 2556-2560; Apr. 2006.
Lizardi et al.; Mutation detection and single-molecule counting using isothermal rolling-circle amplification; Nat. Genet.; 19(3); pp. 225-232; Jul. 1998.
Locascio et al.; Surface chemistry in polymer microfluidic systems; in Lab-on-a-Chip; Elsevier Science; 1st Ed.; pp. 65-82; Oct. 2003.
Loeber; Neonatal screening in Europe; the situation in 2004, Journal of Inherited Metabolic Disease, 30(4), pp. 430-438, Aug. 2007.
Luk et al.; Pluronic Additives: A Solution to Sticky Problems in Digital Microfluidics, Langmuir, 24(12), pp. 6382-6389, Jun. 2008.
Luk et al; A digital microfluidic approach to proteomic sample processing; Analytical Chemistry; 81(11); pp. 4524-4530; Jun. 2009.
Mag et al., Synthesis and selective cleavage of an oligodeoxynucleotide containing a bridged internucleotide 5'-phosphorothioate linkage, Nucleic Acids Res., 19(7), pp. 1437-1441, Apr. 1991.
Makamba et al.; Surface modification of poly(dimethylsiloxane) microchannels; Electrophoresis; 24(21); pp. 3607-3619; Nov. 2003.
Malloggi et al.; Electrowetting—A versatile tool for controlling microdrop generation, Eur. Phys. J. E, 26(1), pp. 91-96, May 2008.
Mandl et al.; Newborn screening program practices in the United States: notification, research, and consent, Pediatrics, 109(2), pp. 269-273, Feb. 2002.
Maroney et al.; A Rapid, quantitative assay for direct detection of microRNAs and other small RNAs using splinted ligation; RNA; 13(6); pp. 930R936; Jun. 2007.

(56) References Cited

OTHER PUBLICATIONS

Maroney et al.; Direct detection of small RNAs using splinted ligation; Nat. Protocols3(2); pp. 279-287; Jan. 2008.

Martinez et al., Simple Telemedicine for Developing Regions: Camera Phones and Paper-Based Microfluidic Devices for Real-Time, Off-Site Diagnosis, Anal. Chem., 80(10), pp. 3699-3707, May 2008.

Martinez et al., Three-dimensional microfluidic devices fabricated in layered paper and tape, PNAS, 105(50), pp. 19606-19611, Dec. 2008.

Martinez et al.; Patterned paper as a platform for inexpensive low-volume, portable bioassays, Angewandte Chemie, 46(8), pp. 1318-1320, Feb. 2007.

Matern et al.; Reduction of the false-positive rate in newborn screening by implementation of MS/MS-based second-tier tests: the Mayo Clinic experience (2004-2007), Journal of Inherited Metabolic Disease, 30(4), pp. 585-592, Aug. 2007.

Mauney, Thermal Considerations for Surface Mount Layouts, in Texas Instruments Portable Power Supply Design Seminar, 16 pgs., 2006.

MEGA; Heterogenous ion-exchange membranes Ralex; 3 pgs.; retrieved Mar. 1, 2016 from the internet: http://www.mega.cz/heterogenous-ion-exchange-membranes-ralex.html.

Meier et al., The photochemistry of stilbenoid compounds and their role in materials technology, Chem. Int. Ed. Engl., 31(11), pp. 1399-1420; Nov. 1992.

Mellors et al.; Fully Integrated Glass Microfluidic Device for Performing High-Efficiency Capillary Electrophoresis and Electrospray Ionization Mass Spectrometry, Analytical Chemistry, 80(18), pp. 6881-6887 (Author Manuscript, 18 pgs.), Sep. 2008.

Michigan Dept. of Community Health; Specimen collection procedure from Michigan Newborn Screening Program, 37 pgs., (retrieved Feb. 19, 2017 online: http://web.archive.org/web/20100715000000*/http://www.michigan.gov/documents/Bloodco2_60773_7.pdf) Jul. 2009.

Miller et al.; A digital microfluidic approach to homogeneous enzyme assays, Anal. Chem., 80(5), pp. 1614-1619, Mar. 2008.

Millington et al.; Tandem mass spectrometry: a new method for acylcarnitine profiling with potential for neonatal screening for inborn errors of metabolism, Journal of Inherited Metabolic Disease, 13(3), pp. 321ý324, May 1990.

Millington et al.; The Analysis of Diagnostic Markers of Genetic Disorders in Human Blood and Urine Using Tandem Mass Spectrometry With Liquid Secondary Ion Mass Spectrometry, International Journal of Mass Spectrometry, 111, pp. 211-228, Dec. 1991.

Mitchell et al.; Circulating microRNAs as stable blood-based markers for cancer detection; Proc Nat Acad Sci; 105(30); pp. 10513-10518; Jul. 2008.

Nakamura et al.; Simple and accurate determination of CYP2D6 gene copy number by a loop-mediated isothermal amplification method and an electrochemical DNA chip; Clinica Chimica Acta; 411(7-8); pp. 568-573; Apr. 2010.

Nelson et al., Incubated protein reduction and digestion on an EWOD digital microfluidic chip for MALDI-MS, Analytical Chemistry, 82(23), pp. 9932-9937, Dec. 2010.

Newborn Screening Ontario, The newborn screening ontario unsatisfactory sample indicator (educational resource), 3 pgs., retrieved online: https://www.newbornscreening.on.ca/en/health-care-providers/submitters/report-cards/nso_unsatisfactory_sample_indicator_jan_2017, (web address was available to applicant(s) at least as of Jan. 2010).

Nilsson et al.; RNA-templated DNA ligation for transcript analysis; Nucl. Acid Res.; 29(2); pp. 578-581; Jan. 2001.

Notomi et al.; Loop-mediated isothermal amplification of DNA; Nucleic Acid Research; 28(12); p. e63 (7 pgs.); Jun. 2000.

Okubo et al.; Liquid-liquid extraction for efficient synthesis and separation by utilizing micro spaces. Chemical Engineering Science, 63(16), pp. 4070-4077, Aug. 2008.

Padilla et al.; Newborn screening in the Asia Pacific region, Journal of Inherited Metabolic Disease, 30(4), pp. 490-506, Aug. 2007.

Paik et al., Coplanar digital microfluidics using standard printed circuit board processes, in Proceedings 9th Int'l Conf Miniaturized Systems for Chemistry and Life Sciences (MicroTAS 2005), Boston, MA, USA, pp. 566-568, Oct. 9-13, 2005.

Parida et al.; Rapid detection and differentiation of Dengue virus serotypes by a real-time reverse transcription-loop-mediated isothermal amplification assay; J Clinical Microbiology; 43(6); pp. 2895-2903; Jun. 2005.

Pauwels et al., Biological-Activity of New 2-5a Analogs, Chemica Scripta, 26 (1), pp. 141-145, Mar. 1986.

Peltonen et al.; Printed electrodes on tailored paper enable electrochemical functionalizationm. of paper; Tappi Nanotechnology Conference; Espoo, Finland; 20 pgs.; Sep. 2010.

Peterschmitt et al.; Reduction of false negative results in screening of newborns for homocystinuria, New England Journal of Medicine, 341(21), 1572-1576, Nov. 1999.

Pitt et al.; Hormone replacement therapy for osteoporosis. Lancet, 335(8695), p. 978, Apr. 1990.

Provincial Health Services Authority (British Columbia Perinatal Health Program), Perinatal Services BC Neonatal Guideline 9: Newborn Screening, 29 pgs., (retrieved Feb. 9, 2017 online: http://www.perinatalservicesbc.ca/health-professionals/guidelines-standards/newborn) guideline revised: Dec. 2010.

Rahhal et al.; The impact of assay sensitivity in the assessment of diseases and disorders in children. Steroids, 73(13), pp. 1322-1327, Dec. 2008.

Rashad; Clinical applications of tandem mass spectrometry: ten years of diagnosis and screening for inherited metabolic diseases, Journal of Chromatography B: Biomedical Sciences and Applications, 758(1), pp. 27-48, Jul. 2001.

Rashed et al.; Diagnosis of inborn errors of metabolism from blood spots by acylcarnitines and amino acids profiling using automated electrospray tandem mass spectrometry, Pediatric Research, 38(3), 324-331, Sep. 1995.

Rawls, Optimistic About Antisense: Promising clinical results and chemical strategies for further improvements delight antisense drug researchers; Chemical & Engineering News; 75(22); pp. 35-39; Jun. 2, 1997.

Ren et al., Automated on-chip droplet dispensing with volume control by electro-wetting actuation and capacitance metering, Sens. Actuator B Chem., 98(2-3), pp. 319-327, Mar. 2004.

Ren et al.; Design and testing of an interpolating mixing architecture for electrowetting-based droplet-on-chip chemical dilution; 12th International Conference on Transducers, Solid-State Sensors, Actuators and Microsystems; vol. 2; Boston, MA, USA; pp. 619-622; Jun. 8-12, 2003.

Ro et al.; Poly (dimethylsiloxane) microchip for precolumn reaction and micellar electrokinetic chromatography of biogenic amines, Electrophoresis, 23(7-8), pp. 1129-1137, Apr. 2002.

Roman et al.; Fully integrated microfluidic separations systems for biochemical analysis, J. Chromatogr. A, 1168(1-2), pp. 170-188, Oct. 2007.

Roman et al.; Sampling and Electrophoretic Analysis of Segmented Flow Streams in a Microfluidic Device, Anal. Chem., 80(21), pp. 8231-8238 (author manuscript, 19 pgs.), Nov. 2008.

Sahai et al.; Newborn screening, Critical Reviews in Clinical Laboratory Sciences, 46(2), pp. 55-82, (online) Mar. 2009.

Sanghvi & Cook (Ed.); Carbohydrate Modifications in Antisense Research; Chapters 2 and 3, American Chemical Society, Washington DC; (207th National Meeting of the American Chemical Society Mar. 13-17, 1994, San Jose, CA); Dec. 1994.

Sanghvi & Cook (Ed.); Carbohydrate Modifications in Antisense Research; Chapters 6 and 7, American Chemical Society, Washington DC; (207th National Meeting of the American Chemical Society Mar. 13-17, 1994, San Jose, CA); Dec. 1994.

Santen et al.; Superiority of gas chromatography/tandem mass spectrometry assay (GC/MS/MS) for estradiol for monitoring of aromatase inhibitor therapy. Steroids. 72(8), pp. 666-671, Jul. 2007.

Sasano et al.; From Endocrinology to Intracrinology. Endocr Pathol, 9(1), pp. 9-20, Spring 1998.

Satoh et al.; Electrowetting-based valve for the control of the capillary flow, J. Appl. Phys., 103(3), 034903, Feb. 2008.

(56) References Cited

OTHER PUBLICATIONS

Satoh et al.; On-chip microfluidic transport and mixing using electrowetting and incorporation of sensing functions, Anal. Chem., 77(21), pp. 6857-6863, Nov. 2005.
Sawai et al., Synthesis and properties of oligoadenylic acids containing 2?-5? phosphoramide linkage, Chem. Lett., 13(5), pp. 805-808, May 1984.
Schertzer et al.; Using capacitance measurements in EWOD devices to identify fluid composition and control droplet mixing; Sens. Actuators B; 145(1); pp. 340-347; Mar. 2010.
SCRIVER_Commentary; A Simple Phenylalanine Method for Detecting Phenylketonuria in Large Populations of Newborn Infants by Guthrie et al., Pediatrics, 32(3), 338-343, Sep. 1963.
Shih et al., A feedback control system for high-fidelity digital microfluidics, Lab Chip, 11(3), pp. 535-540, Feb. 2011.
Simpson et al.; Estrogen—the Good, the Bad, and the Unexpected. Endocr Rev, 26(3), pp. 322-330; May 2005.
Sinton et al.; Electroosmotic velocity profiles in microchannels, Colloids Surf. A, 222(1-3), pp. 273-283, Jul. 2003.
Skendzel, Rubella immunity: Defining the level of protective antibody, Am. J. Clin. Pathol., 106(2), 170-174, Aug. 1996.
Smith et al; Diagnosis and Management of Female Infertility. Journal of the American Medical Association 290(13), pp. 1767-1770, Oct. 2003.
Sooknanan et al., Nucleic Acid Sequence-Based Amplification, Ch. 12; Molecular Methods for Virus Detection (1st Ed.), Academic Press, Inc., pp. 261-285; Jan. 1995.
Sprinzl et al., Enzymatic incorporation of ATP and CTP analogues into the 3' end of tRNA, Eur. J. Biochem., 81(3), pp. 579-589, Dec. 1977.
Srinivasan et al.; An integrated digital microfluidic lab-on-a-chip for clinical diagnostics on human physiological fluids, Lab Chip, 4(4), pp. 310-315, Aug. 2004.
Stanczyk et al.; Standardization of Steroid Hormone Assays Why, How, and When?, Cancer Epidemiol Biomarkers Prey, 16(9), pp. 1713-1719, Sep. 2007.
Steckl et al.; Flexible Electrowetting and Electrowetting on Flexible Substrates; Proc. SPIE 7956; Advances in Display Technologies; and E-papers and Flexible Displays; 795607 (6 pgs.); Feb. 2011.
Stegink et al.; Plasma amino acid concentrations and amino acid ratios in normal adults and adults heterozygous for phenylketonuria ingesting a hamburger and milk shake meal, American Journal of Clinical Nutrition, 53(3), pp. 670-675, Mar. 1991.
Svoboda et al.; Cation exchange membrane integrated into a microfluidic device; Microelectronic Engineering; 86; pp. 1371-1374; Apr.-Jun. 2009.
Szarewski et al.; Contraception. Current state of the art. British Medical Journal, 302(6787), pp. 1224-1226, May 1991.
Szymczak et al.; Concentration of Sex Steroids in Adipose Tissue after Menopause. Steroids, 63(5-6), pp. 319-321, May/Jun. 1998.
Tachibana et al.; Application of an enzyme chip to the microquantification of L-phenylalanine, Analytical Biochemistry, 359(1), pp. 72-78, Dec. 2006.
Teh et al.; Droplet microfluidics, Lab Chip, 8(2), pp. 198-220, Feb. 2008.
Therrell et al.; Newborn screening in North America, Journal of Inherited Metabolic Disease, 30(4), pp. 447-465, Aug. 2007.
Tomita et al.; Loop-mediated isothermal amplification (LAMP) of gene sequences and simple visual detection of products; Nature Protocols; 3(5); pp. 877-882; (online) Apr. 2008.
Turgeon et al.; Combined Newborn Screening for Succinylacetone, Amino Acids, and Acylcarnitines in Dried Blood Spots, Clinical Chemistry, 54(4), pp. 657-664, Apr. 2008.
Udenfriend et al.; Fluorescamine: a reagent for assay of amino acids, peptides, proteins, and primary amines in the picomole range, Science, 178(4063), pp. 871-872, Nov. 1972.
Univ. of Maryland—Baltimore Washington Medical Center; Plasma amino acids, 6 pgs., retrieved Feb. 10, 2017 from: http://www.mybwmc.org/library/1/003361, Web address available to applicant(s) at least as of Jan. 2010.
Verkman; Drug Discovery in Academia; Am J Physiol Cell Physiol; 286(3); pp. C465-C474; Feb. 2004.
Walker et al.; A Chemiluminescent DNA Probe Test Based on Strand Displacement Amplification (Chapter 15); Molecular Methods for Virus Detection (1st Ed.), Academic Press, Inc., pp. 329-349; Jan. 1995.
Walker et al.; A passive pumping method for microfluidic devices, Lab Chip, 2(3), pp. 131-134, Aug. 2002.
Washburn et al.; Large-scale analysis of the yeast proteome by multidimensional protein identification technology, Nat. Biotechnol., 19(3), pp. 242-247, Mar. 2001.
Watson et al.; Multilayer hybrid microfluidics: a digital-to-channel interface for sample processing and separations; Anal. Chem.; 82(15); pp. 6680-6686; Aug. 2010.
Wu et al.; Design, Simulation and Fabrication of Electrowetting-Based Actuators for Integrated Digital Microfluidics; Proceedings of the 1st IEEE International Conference on Nano/Micro Engineered and Molecular Systems; Zhuhai, China; pp. 1097-1100; Jan. 18-21, 2006.
Wu et al.; Electrophoretic separations on microfluidic chips, J. Chromatogr. A, 1184(1-2), pp. 542-559, Mar. 2008.
Yi et al.; Spangler et al., Eds; Channel-to-droplet extractions for on-chip sample preparation, in Proceedings of Solid-State Sensor, Actuator and Microsystems Workshop, pp. 128-131, Jun. 2006.
Yoon et al.; Preventing Biomolecular Adsorption in Electrowetting-Based Biofluidic Chips; Anal Chem; 75; pp. 5097-5102; Aug. 2003.
Yoon; Open-Surface Digital Microfluidics; The Open Biotechnology Journal; 2(1); pp. 94-100; Apr. 2008.
Young et al.; Calculation of DEP and EWOD Forces for Application in Digital Microfluidics, J. Fluids Eng., 130(8), pp. 081603-1-081603-9, Jul. 2008.
Zaffanello et al.; Multiple positive results during a neonatal screening program: a retrospective analysis of incidence, clinical implications and outcomes, Journal of Perinatal Medicine, 33(3), pp. 246-251, May 2005.
Zhao et al., Lab on Paper, Lab Chip, 8(12), pp. 1988-1991, Dec. 2008.
Znidarsic-Plazl et al.; Steroid extraction in a microchannel system—mathematical modelling and experiments. Lab Chip, 7(7), pp. 883-889, Jul. 2007.
Zuker; Mfold Web Server for Nucleic Acid Folding and Hybridization Prediction; Nucleic Acid Research ; 31(13); pp. 3406-3415; Jul. 2003.
Zytkovicz et al.; Tandem mass spectrometric analysis for amino, organic, and fatty acid disorders in newborn dried blood spots: a two-year summary from the New. England Newborn Screening Program, Clinical Chemistry, 47(11), pp. 1945-1955, Nov. 2001.
Fobel et al.; U.S. Appl. No. 15/457,930 entitled "Printed Digital Microfluidic Devices Methods of Use and Manufacture Thereof", filed Mar. 13, 2017.
Jebrail et al.; U.S. Appl. No. 15/579,455 entitled "Air-matrix digital microfliuidics aparatuses and methods for limiting evaporation and surface fouling," filed Dec. 4, 2017.
Jebrail et al.; U.S. Appl. No. 15/579,239 entitled "Evaporation management in digital microfluidic devices," filed Dec. 4, 2017.
Li et al.; Test structure for characterizing low voltage coplanar EWOD system; IEEE Transaction on Semiconductor Manufacturing; IEEE Service Center; Piscataway, NJ.; 22(1); pp. 88-95; Feb. 4, 2009.
Paneri et al.; Effect of change in ratio of electrode to total pitch length in EWOD based microfluidic system; InComputer Applications and Industrial Electronics (ICCAIE); 2010 International Conference; pp. 25-28; Dec. 5, 2010.
Sabourin et al.; Interconnection blocks: a method for providing reusable, rapid, multiple, aligned and planar microfluidic interconnections; Journal of Micromechanics and Microengineering; 19(3); 10 pages; doi:10.1088/0960-1317/19/3/035021; Feb. 18, 2009.

* cited by examiner a)

b)

(a)

(b)

(c)

METHOD OF PROCESSING DRIED SAMPLES USING DIGITAL MICROFLUIDIC DEVICE

CROSS-REFERENCE TO RELATED APPLICATION

This application is a National Phase application claiming the benefit of PCT/CA2011/050205 filed on Apr. 15, 2011 in English, which further claims priority to U.S. Provisional Application No. 61/331,679, titled "METHOD OF DIGITAL MICROFLUIDIC SAMPLE PREPARATION FOR MASS ANALYSIS OF METABOLIC DISORDERS" and filed on May 5, 2010, the entire contents of which are incorporated herein by reference.

BACKGROUND

This invention relates to methods of processing of dried samples for subsequent analysis. Blood samples stored as dried blood spots have emerged as a useful sampling and storage vehicle for clinical and pharmaceutical analysis in a wide range of applications. For example, the Newborn Screening Ontario facility at the Children's Hospital of Eastern Ontario evaluates dried blood spot samples from approximately 140,000 babies each year for 28 inherited diseases. In each screening test, a dried blood spot sample is collected and then mailed to facility for analysis by tandem mass spectrometry (MS/MS). Unfortunately, this technique is slowed by an extensive sample preparation regimen (including excision/punching, extraction, evaporation, resolubilization, and derivatization), and in addition, high-throughput screening typically requires robotic sample handling.

The success of dried blood spot sampling and MS/MS for newborn screening has led to a surge in popularity for similar techniques for a wide spectrum of applications in clinical labs and the pharmaceutical industry. Dried blood spot sampling methods allow for the collection of small amounts of sample and are convenient for long-term storage and cataloguing. MS/MS methods allow for the unambiguous identification and quantification of many different analytes in a single shot.

Unfortunately, the throughput and turn-around-time associated with this technique are problematic as a result of time-consuming sample preparation. In particular, the off-line sample preparation of blood spots on filter paper necessitates the labor intensive and time consuming steps of extraction via centrifugation, in which the analyte is obtained in a supernatant. Furthermore, the maintenance of instruments (sample preparation robots and mass spectrometers) and plumbing (capillary tubes and associated connections) requires many hours of laboratory-time, which reduces the throughput of such analyses. In addition, the costs are magnified by the scale of operation (for example, nearly 150,000 samples are processed a year in Ontario alone).

SUMMARY

Methods are provided for the preparation of a sample using a digital microfluidic platform and the optional subsequent mass analysis of an extracted analyte. A sample is dried, optionally on a solid phase support, and contacted with digital microfluidic array. An analyte present within the dried sample is extracted into an extraction solvent by electrically addressing the digital microfluidic array to transport a droplet of extraction solvent to the dried sample spot. The extracted sample may be dried and subsequently processed on the digital microfluidic array for derivatization. The digital microfluidic device may further include an integrated microfluidic channel having an output aperture, and the method may further include contacting a droplet containing extracted analyte with the microfluidic channel and applying a suitable electric field for generating nano-electrospray, thereby enabling the device to be directly interfaced with a mass analysis device.

Accordingly, in one aspect, there is provided a method of sample preparation comprising the steps of: providing a solid phase support comprising a dried sample; providing the solid phase support at a first location between an upper plate and a lower plate of a two-plate digital microfluidic device, wherein the first location is dropwise addressable under actuation of the digital microfluidic device; providing an extraction solvent at an additional location that is dropwise addressable under actuation of the digital microfluidic device; actuating the digital microfluidic device to transport a droplet of the extraction solvent to the first location; and incubating the droplet of the extraction solvent and extracting an analyte in the dried sample.

A further understanding of the functional and advantageous aspects of the invention can be realized by reference to the following detailed description and drawings.

BRIEF DESCRIPTION OF THE DRAWINGS

Embodiments will now be described, by way of example only, with reference to the drawings, in which:

FIG. 3(a) shows the individual layers forming the device, and FIG. 3(b) shows the integrated device.

DETAILED DESCRIPTION

As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to methods of processing dried samples using a digital microfluidic device.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

As used herein, the terms "about" and "approximately, when used in conjunction with ranges of dimensions of particles, compositions of mixtures or other physical properties or characteristics, is meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present invention.

As used herein, the term "exemplary" means "serving as an example, instance, or illustration," and should not be construed as preferred or advantageous over other configurations disclosed herein.

In a first embodiment, a method of sample preparation is provided in which a digital microfluidic array is employed to extract and prepare an analyte for subsequent analysis. The sample preparation method is especially suitable for use with a subsequent mass analysis step such as a tandem mass spectrometry.

Figure 1:
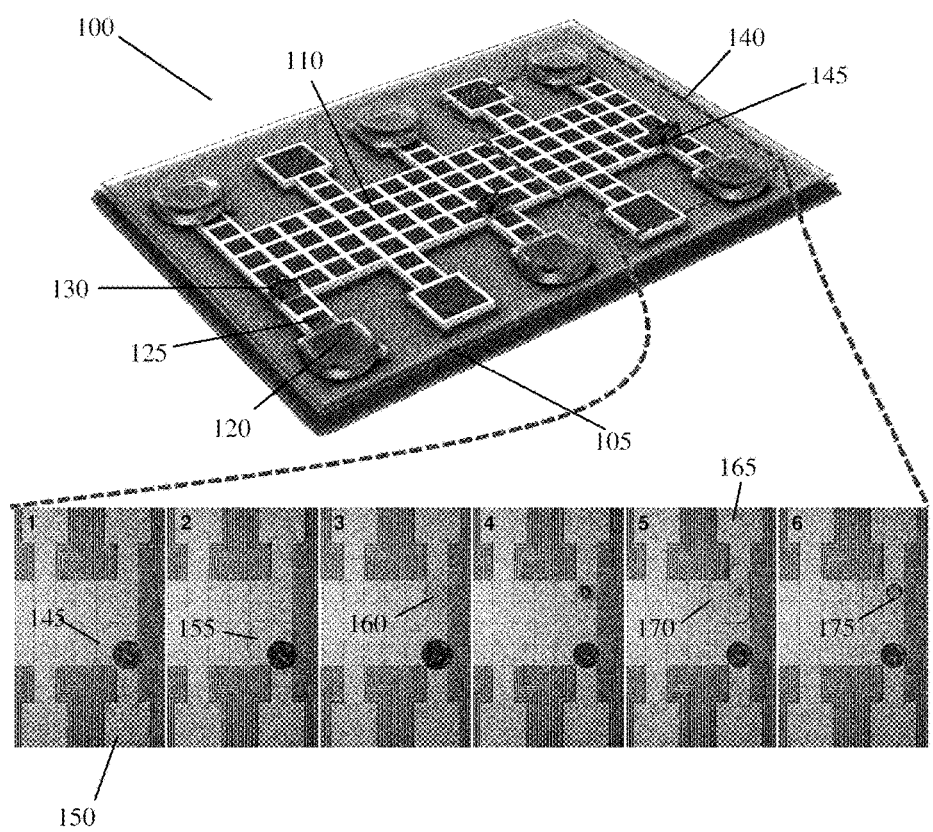
FIG. 1 illustrates steps in sample processing by digital microfluidics. The top image is a schematic of a digital microfluidic device which allows for the processing of 3 blood samples simultaneously. The bottom image is a sequence of frames from a movie (left-to-right) depicting several stages in sample processing including: (1) a dried blood sample; (2) mixing and incubating an extracted droplet with the sample; (3) a droplet containing sample extricate after translation away from the dried sample; (4) a dried extract; (5) mixing and incubating a derivatization reagent droplet with the dried extract; and (6) the dried, derivatized product.

FIG. 1 illustrates a digital microfluidic device 100 for performing a method according to a first embodiment. The device 100 includes an insulating substrate 105 having formed thereon an array 110 of digital microfluidic elements that can be electrically actuated to transport droplets between array elements. The array elements each include a conductive surface that is coated with a hydrophobic insulator. For example, the device may be formed on a glass substrate, onto which patterned chromium electrodes are formed by photolithography and etching, and coated with Parylene-C and TEFLON-AF.

Each element is electrically connected to a contact pad (not shown) for electrically addressing the array. The array may further include reagent reservoirs 120 that are suitable for containing a reagent volume. An array element 125 adjacent to a reservoir may be actuated to form reagent droplets and transport the reagent droplets to samples 130 within the array. As shown in FIG. 1, the digital microfluidic array 110 may include multiple regions in which various samples may be processed in parallel. Additionally, side walls and a top plate may also be provided for forming a dual-layer device, in which array elements may be actuated based on a voltage difference between the array and an electrode on the top plate electrode. For example, the top plate may be transparent and may comprise an unpatterned indium tin oxide (ITO) coated glass substrate coated with a hydrophobic material such as TEFLON-AF™.

The bottom portion of FIG. 1 provides a series of images from a movie illustrating an example of the present embodiment, in which an amino acid analyte is extracted from a dried blood spot and derivatized for a subsequent mass analysis assay. As shown in the Figure, the images correspond to a single region 140 of the illustrated digital microfluidic device 100.

In image 1 in the bottom portion of FIG. 1, a droplet of blood is provided to the digital microfluidic array and dried to form a dried blood spot 145. It is to be appreciated that the sample may be dispensed directly onto the array, or may be dispensed onto a sample reservoir and the array may be electrically addressed to extract a droplet from the sample reservoir and transport the droplet to an element of the array.

An extraction solvent is then provided to the array, and may be provided by dispensing the extraction solvent to an extraction solvent reservoir 150. As shown in image 2, the array is then electrically addressed to transport one or more droplets 155 of extraction solvent to the dried blood spot. The extraction solvent is incubated (it has been found that approximately 5 to 10 min is sufficient to incubate the extraction solvent) over the dried blood spot and analyte present in the dried blood spot is extracted into the extraction solvent. It will be understood that a suitable incubation time to extract the analyte may depend on the properties of the analyte and extraction solvent. In image 3, the array is again electrically actuated to transport the extraction solvent to a second array element 160, where it is subsequently dried, as shown in image 4.

In image 5, the array is electrically addressed to transport one or more droplets 170 of a derivatization reagent from reagent reservoir 165 to the second array element 160. The derivatization reagent is incubated (for example, for approximately 5 to 10 min) to solubilize and derivative the analyte previously dried onto second element 160. It will be understood that a suitable incubation time to solubilize and derivative the analyte may depend on the properties of the analyte and the derivatization solvent. In image 6, the derivatization reagent droplet is evaporated to provide a dried derivatized analyte spot 175.

Although embodiments disclosed herein illustrate various methods using blood as the sample matrix, it is to be understood that the sample need not be blood, and may be or may include any suitable sample matrix, such as, but not limited to, whole blood, serum, plasma, urine, sputum, and cerebral spinal fluid.

Figure 2:
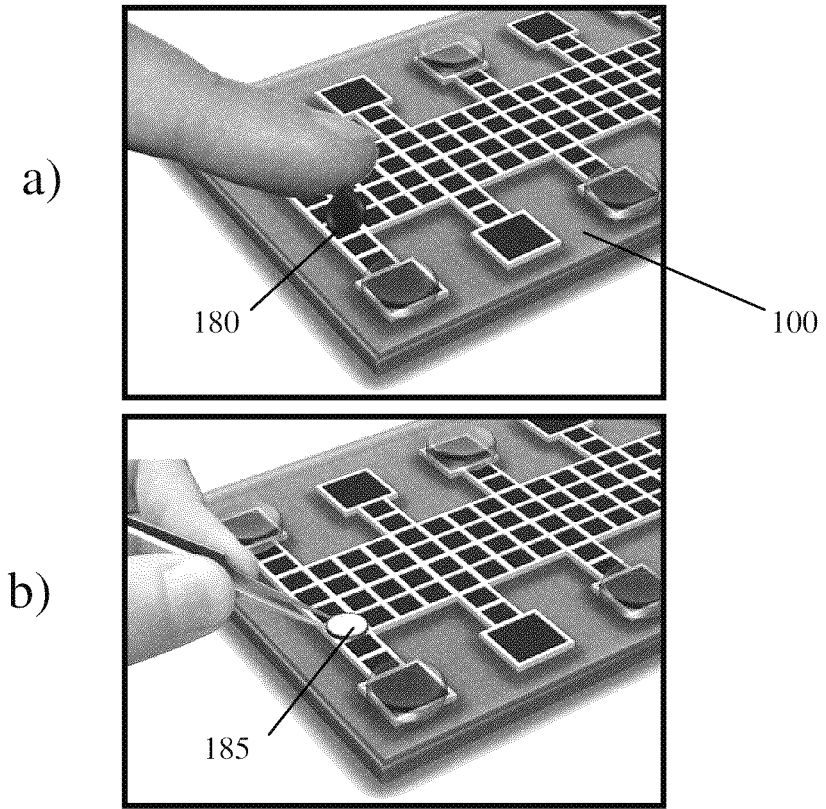
FIG. 2 illustrates three digital microfluidic methods for processing different sample formats, where (a) shows a droplet of blood spotted directly onto the device surface and allowed to dry, (b) In method 2 shows a punch from filter paper bearing dried blood that is positioned on the device surface.

For example, as shown in FIG. 2(*a*), a sample 180 could be spotted directly and dried onto a digital microfluidic device 100 at the point of collection, after which the device could be directly processed or transported to a remote testing location for analysis. If the sample is spotted directly onto the device, it is necessary for the device to be provided at the point of collection. This may be achieved by providing only a component of the device, such as the bottom plate of a two-plate digital microfluidic device. After having received the spotted plate at the laboratory, the full device could be assembled and electrically connected to a device controller. It is to be understood that embodiments involving sample spots dried directly onto the surface of a digital microfluidic array device may be performed using a single plate digital microfluidic device, or a two-plate microfluidic device.

Alternatively, the sample may be spotted onto a solid phase support, such as an exchangeable carrier or exchangeable sheet, as disclosed in International Patent Application No. PCT/EP2009/062657, titled "EXCHANGEABLE CARRIERS PRE-LOADED WITH REAGENT DEPOTS FOR DIGITAL MICROFLUIDICS", and filed on Sep. 30, 2009, Publication No. WO2010037763 A1, which is incorporated herein by reference in its entirety. The exchangeable carrier is an electrically insulating sheet having a hydrophobic surface, where the insulating sheet may be contacted with a digital microfluidic array device to form an external surface of the device. After contacting the exchangeable carrier with the digital microfluidic array, the digital microfluidic array may be actuated to transport droplets that are provided on or in contact with the exchangeable carrier. This allows for repeated use of the device without requiring device disposal or decontamination of the device surface.

Although PCT/EP2009/062657, Publication No. WO2010037763 A1, disclosed the use of a exchangeable carrier for providing a exchangeable device component including dried reagents, the exchangeable sheets may additionally or alternatively employed to remotely obtaining a dried sample and providing the dried sample to another location (such as a laboratory) for testing. The sample is dried and spotted onto the exchangeable carrier prior to device assembly. The sample is dried at a location such that the dried sample spot is accessible to droplets actuated over the front hydrophobic surface of the exchangeable sheet after attachment to the digital microfluidic device. The dispensing of the sample onto an appropriate location of the exchangeable carrier may be achieved using alignment marks or features, or, for example, using an external masking device that places an aperture at the appropriate location to guide the dispensing process. The exchangeable carrier may also include dried reagents at one or more pre-selected positions, where the positions are selected to be accessible to droplets actuated over the front hydrophobic surface of the exchangeable carrier after attachment to the digital microfluidic device. The exchangeable carrier with a dried spot on a surface thereof may be applied to the surface of a single plate digital microfluidic device, or to the channel-facing surface of one or both of the top and bottom plates of a two-plate digital microfluidic device.

In an alternative embodiment, the sample may be first dried onto a solid phase support, after which at least a portion of the solid phase support is locally contacted with a location on the digital microfluidic for analyte extraction and optional further sample processing steps. This allows for the remote collection of dried sample in a simple and convenient format for subsequent processing with a digital microfluidic device.

An example of this embodiment is shown in FIG. 2(*b*), where a filter paper punch 185 bearing dried blood is contacted with a surface of a microfluidic device at a location that is dropwise accessible under actuation of the digital microfluidic device. In FIG. 2(*b*), the filter paper punch is positioned over a digital microfluidic element and contacted with the surface of the first plate as shown. Prior to processing the sample, the top plate of the digital microfluidic device is installed to complete the assembly of the two-plate device (as described above, a gap or channel is formed by a spacer layer provided between the upper and lower plates of the digital microfluidic device). This method allows for the convenient placement of the solid phase support at any internal addressable location of the digital microfluidic array. Alternatively, a two-plate digital microfluidic device may be pre-assembled, and the filter paper punch may be inserted into the gap between the two plates of the digital microfluidic device and positioned at a pre-determined location that is dropwise addressable by the digital microfluidic array. Any of the surfaces of the digital microfluidic array may be initially contacted with a exchangeable carrier, and the solid phase support may contact the digital microfluidic device indirectly through contact with the exchangeable carrier.

After having provided the solid phase support at a suitable location between the upper and lower plates of the digital microfluidic device, where the suitable location is in accessible to droplets actuated by the digital microfluidic device, the digital microfluidic array may be actuated to transport one or more extraction solvent droplets to the location of the solid phase support for incubation and extraction of the dried analyte. The extraction and other sample processing steps, such as derivatization of the extracted analyte, may further be performed as described above.

The solid phase support has a thickness that is selected to be compatible with droplet actuation in a digital microfluidic device. For example, a suitable thickness range for a two-plate digital microfluidic device is approximately 90 to 450 microns. As noted above, a suitable solid phase is filter paper, which has a thickness that is compatible with digital microfluidic devices. Other suitable solid phase supports include other porous materials, such as, but not limited to, paper, cellulose filters, nitrocellulose, polymer based monoliths such as porous polymer monoliths, and hydrogel forming materials. It has been shown (see below) that when a porous solid phase support such as filter paper is sandwiched between two plates of a digital microfluidic device, the support need not be adhered or otherwise fixed to the device, and is held in place after being contacted with a droplet by inherent forces such as capillary forces. In an alternative embodiment, a non-porous solid phase may be employed, for example, as described above in the context of removable carriers. In another embodiment, a punched non-porous solid phase may be adhered or secured to a surface of the digital microfluidic array using one of many suitable techniques, including bonding methods such as thermal bonding and/or gluing. The solid phase support may be selected to have a hydrophobic surface in order to support the transport of a droplet from a location where the droplet is contacting the solid phase support to a location elsewhere on the digital microfluidic array.

Figure 10:
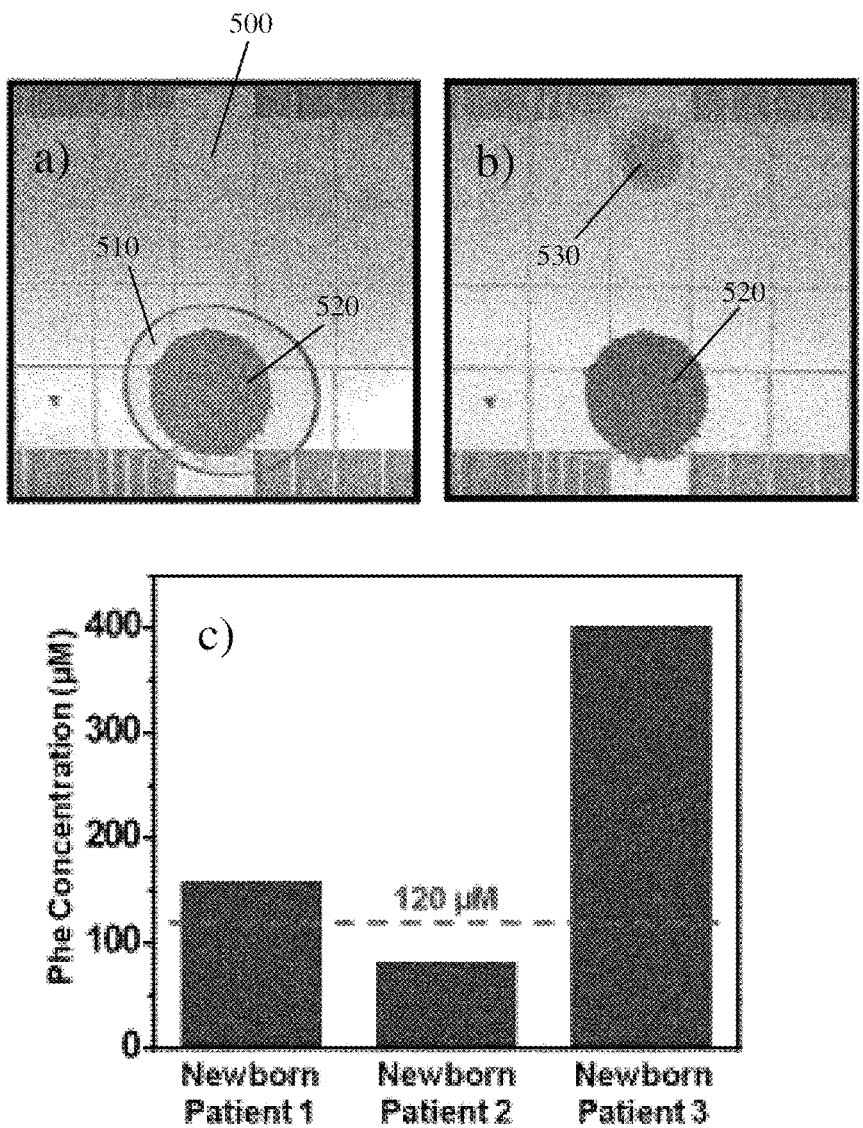
FIG. 10 illustrates the analysis of amino acids in dried blood spots by digital microfluidic methods, where (a) and (b) show frames from a movie depicting sample processing of 3.2 mm diameter punch of a dried blood spot on filter paper by digital microfluidics, and (c) provides a graph of Phe concentrations measured by the digital microfluidic method involving punches from three patients.

The lateral extent (e.g. surface area and/or diameter) of the solid phase support is sufficiently small to support the actuation of droplets to and from the solid phase support, In some cases, it may be beneficial to limit the lateral extent of the solid phase support to less than one array element. For example, this can allow the transport of droplets along neighbouring channels without contacting the solid phase support. However, it is to be understood that the lateral extent of the solid phase support need not be smaller than an array element, and the lateral extent of the solid phase support may overlap with neighbouring array elements, as demonstrated in FIG. 10.

For example, a larger lateral extent of the solid phase support will provide a larger radial extent of dried solvent, and a correspondingly higher amount of analyte for extraction. In some applications, it may be desirable to provide a greater number of analyte molecules, particularly in applications where the analyte concentration range of interest is near to the limit of detection of an analytical method employed for subsequent detection.

It may also be useful to provide, on a single digital microfluidic array, multiple solid phase supports, where each solid phase support contains a common dried sample. The multiple solid phase supports may be subjected to extraction steps as described above, where the extraction steps are performed in parallel or in serial format. The extracted analyte from the multiple solid phases may be dried onto a common array element in order to concentrate the extracted analyte.

It another embodiment, multiple solid phase supports may be provided on a single digital microfluidic array, where the solid phase supports contain analyte or analytes from different samples for parallel processing on a single digital microfluidic array. This allows for multiplexed extraction from multiple samples, and is beneficial in further reducing labor costs and turn around time. For example, such an embodiment may be useful for the multiplexed extraction and processing of analyte in applications involving high-throughput screening.

After utilizing the digital microfluidic array for the extraction and derivatization of the analyte as described above (either using direct sample deposition and drying or indirect dried sample processing), an assay for the analyte may be subsequently performed using a mass analyzer. To prepare the derivatized analyte for mass analysis, the derivatized analyte is resuspended in a solvent compatible with the subsequent mass analysis step.

The extraction solvent may additionally contain an internal standard for use with the subsequent mass analysis step. The standard may include a concentration of isotopically labeled analyte. The mass analysis may involve analysis by collision-induced dissociation for tandem mass analysis. In another embodiment, the resuspended analyte may be first provided to a chromatographic separation system (such as a high performance liquid chromatography system) prior to subsequent analysis of the separation system eluent with a mass analysis device.

Figure 3:
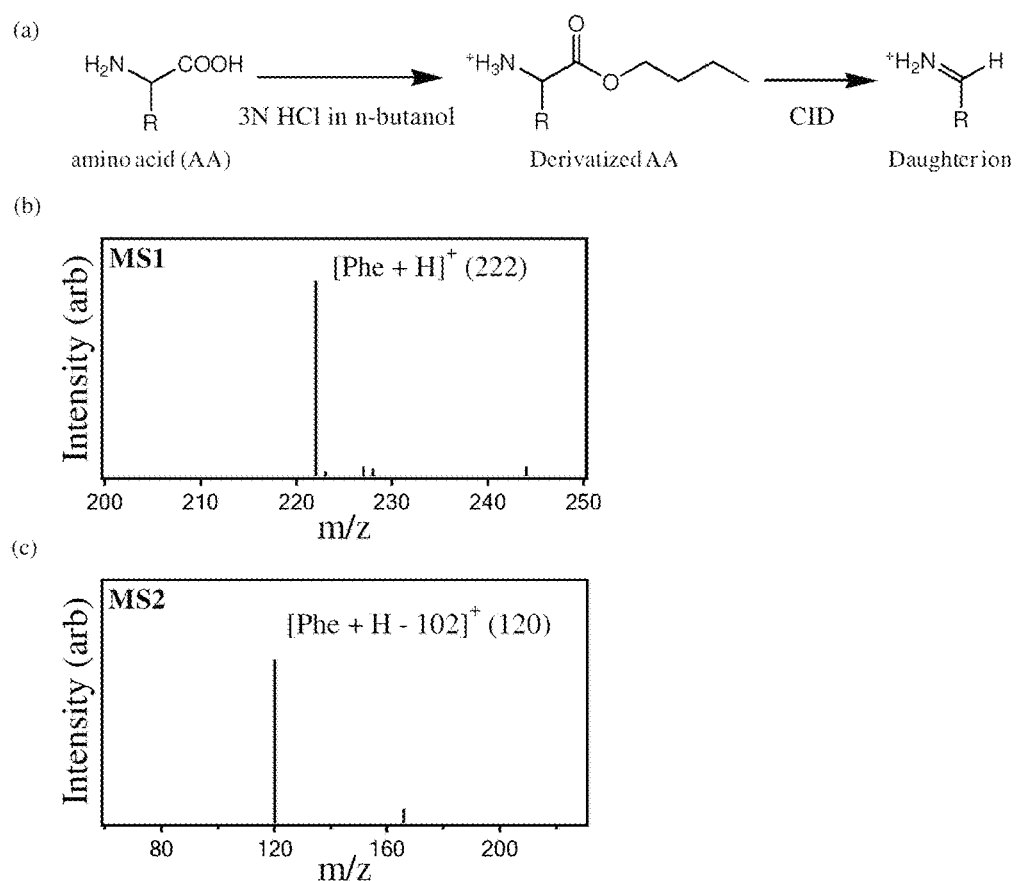
FIG. 3 illustrates the steps in processing blood samples for quantification of amino acid by tandem mass spectrometry. (a) Reaction scheme involving derivatization of the extracted amino acid, followed by derivatization with n-butanol, followed by the formation of a daughter ion by collision induced dissociation in the mass spectrometer. (b) Mass spectrum generated from primary analysis of derivatized phenylalanine (Phe). (c) Mass spectrum generated from the secondary analysis of derivatized Phe showing the loss of 102 amu as a result of collision induced dissociation.

In one embodiment, the analyte is one or more amino acids, fatty acids (acylcarnitines), organic acids, and a combination thereof. The extraction solvent in this case is preferably methanol. A suitable derivatization step is illustrated in FIG. 3(*a*) for the non-limiting case of amino acid (amino acid) analyte, in which a derivatization reagent comprising HCl-butanol transforms each amino acid to its corresponding butyl ester (derivatized amino acid), and subsequent formation of daughter ions via collision induced dissociation makes each analyte convenient to quantify by multiple reaction monitoring. The capacity to carry out similar processes in parallel for many different amino acids simultaneously with minimal steps makes the present digital microfluidic and MS/MS method a useful tool for a wide range of applications, including the screening of metabolic disorders on a large scale.

FIGS. 3(*b*) and 3(*c*) provide illustrative primary (MS1) and secondary (MS2) mass spectra for the amino acid, phenylalanine, with peaks at m/z 222 and 120. This technique, using collision induced dissociation and MS/MS, is useful for selectively analysing such species because they exhibit a characteristic loss of butylformate ($HCOOC_4H_9$, 102 D), making them easy to identify.

In one embodiment, more than one extraction step may be performed using the digital microfluidic array for the purpose of extracting multiple analytes that are beneficially processed using different extraction and/or derivatization solvents. In a one embodiment, the multiple extraction methods are performed on a common digital microfluidic platform. The multiple extraction methods may be performed serially using a common dried sample spot or in parallel using two separate dried sample spots, where the dried sample spots may be dried directly onto the digital microfluidic device, or dried onto an intermediate matrix as described above. The final droplets containing the extracted analyte, in which the droplets are provided in a fluid that is compatible with a subsequent mass analysis step, may be combined and provided to the mass analyzer in a single aliquot for multiplexed mass analysis. In a non-limiting example, the marker succinulacetone may be extracted in order to perform an assay for tyrosinemia type I. The extraction method is similar to that discussed above, in which an acidic extraction solvent containing hydrazine is provided to the digital microfluidic array. Preferably, this extraction solvent comprises an acetonitrile/water/formic acid solution having relative concentrations of 80:20:0.1% by volume, respectively, and further containing 0.1% hydrazine monohydrate and isotopically labeled succinylacetone ($^{13}C_5$-succinylacetone), as discussed in Turgeon et al. (C. Turegeon et al., Clin. Chem. 54, 657, 2008). The array is then electrically actuated to transfer a droplet of the extraction solvent to a dried sample (e.g. a dried blood spot), which may have already been processed according to the above protocol using a different solvent (e.g. methanol). The extraction solvent droplet containing the extract succinulacetone is then transported to a different element of the digital microfluidic array under electrical actuation of the array, where it may be dried and resolubilized in another buffer prior to analysis.

In one embodiment, the digital microfluidic device is interfaced a the mass spectrometer to support a method that may be performed without the need for intermediate manual or robotic liquid handling steps. This overcomes many of the difficulties associated with convention nanoflow electrospray ionization (nESI), which is known to be a complex technique requiring operator expertise and vigilance to achieve reproducible results. For example, this limitation is part of the reason why newborn blood samples are often mailed to a single remote screening facility for processing.

Accordingly, in one embodiment, a nESI device is integrated into the microfluidic device to provide a hybrid digital microfluidic and nESI device that may be formed by standard batch-processing. Sample processing is performed as described above, where an analyte is extracted and processed from a dried sample (directly dried onto the digital microfluidic array, or indirectly dried onto a suitable matrix which is contacted with the array), and mass analysis is realized by positioning the hybrid device in front of the mass spectrometer inlet and applying an electrical potential to achieve nESI. This process requires only a few minutes to accomplish and can be implemented by non-experts.

Figure 4:
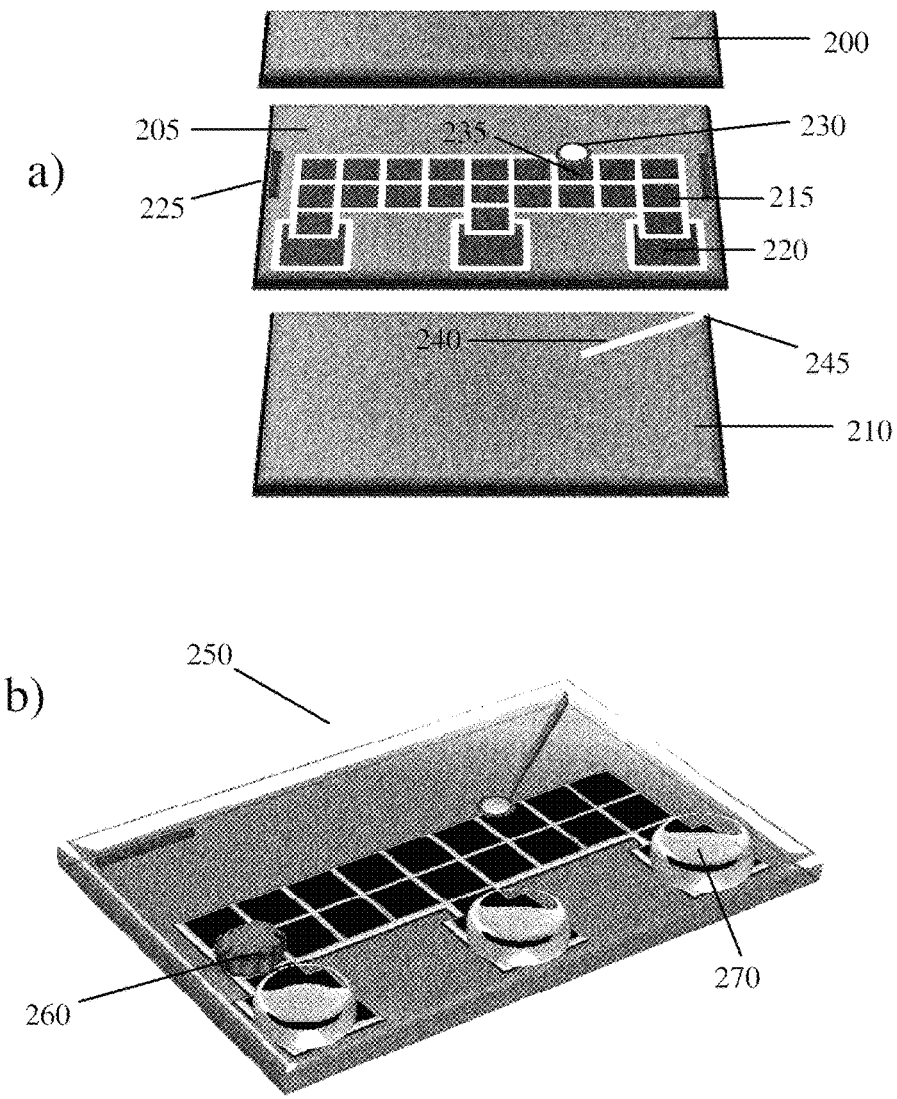
FIG. 4 provides schematics showing the hybrid digital microfluidic device used for in-line mass spectrometry analysis.

Such an integrated system is illustrated in FIG. 4, which shows the various layers that form the device in FIG. 4(a) and the overall integrated device in FIG. 4(b). As shown in FIG. 4(a), the device comprises a top plate 200, a digital microfluidic layer 205, and a microfluidic channel layer 210. Top plate 205 comprises a non-conductive and substrate, having formed on its lower surface an electrode that is further coated with a hydrophobic material. Preferably, top plate is transparent and comprises an unpatterned indium tin oxide (ITO) coated glass substrate coated with a hydrophobic material such as TEFLON-AF™.

Digital microfluidic layer 205 is similar to the digital microfluidic device described above, and comprises an insulating substrate having formed thereon an array 215 of digital microfluidic elements that can be electrically actuated to transport droplets between array elements. Preferably, the array elements each comprise a conductive surface that is coated with a hydrophobic insulator. For example, the device may be formed on a glass substrate, onto which patterned chromium electrodes are formed by photolithography and etching, and coated with Parylene-C and TEFLON-AF. As described above, each element is electrically connected to a contact pad (not shown) for electrically addressing the array. The array preferably further comprises reagent reservoirs 220 that are suitable for containing a reagent volume. Vertical spacing elements 225 are provided between top plate 200 and digital microfluidic layer 205 for forming a planar channel within which fluidic droplets may be transported by electrically addressing the digital microfluidic array.

Digital microfluidic layer 205 further includes a vertical hole 230 located adjacent to array element 235, enabling droplets residing on the digital microfluidic array to be transported to, and contacted with, the aperture of vertical hole 230, whereby hole 230 may be filled under capillary action.

Microfluidic channel layer 210 comprises a microfluidic channel 240 formed in an upper surface of a substrate, and extending to the edge of the substrate. By positioning microfluidic channel layer 210 in contact with the underside of digital microfluidic layer 205 so that an end portion of microchannel 240 is contacted with vertical hole 230, an inlet is formed in microchannel 240 that may be filled by fluid captured by vertical hole 230 under further capillary forces. Accordingly, microfluidic channel 240 may be filled with liquid from a droplet by electrically addressing the digital microfluidic array to transport the droplet to contact vertical hole 230, which leads to the subsequent filling of channel 240 under via capillary forces. The contacting of microfluidic channel layer 210 with digital microfluidic layer 205 also forms an external outlet 245 of microfluidic channel 240. In a preferred embodiment, microfluidic channel outlet 245 is located in the corner of the device. FIG. 4(b) illustrates an integrated device 250 containing a sample droplet 260 and a reagent 270 loaded onto a reagent reservoir.

In another embodiment, the digital microfluidic array is employed to perform a sample preparation method as disclosed above, and the derivatized analyte is solubilized in a fluidic droplet that is compatible with a subsequent mass analysis step. The droplet is transported to contact and fill the microfluidic channel, and the device is positioned in close proximity to the inlet of a mass analysis device. An electrical conductor is then made to contact the liquid in the microchannel, for example, by removing the top plate and placing a wire into the vertical hole 230. Alternatively, a conductor may be made to contact the contents of the microfluidic channel by forming a secondary access hole and inserting the electrical conductor into the secondary hole in such a way as to provide a suitable fluidic seal, thereby preventing leakage from the microchannel. Electrospray may be subsequently generated in a cone emerging from outlet 245 by applying a voltage between the conductor and the inlet of the mass analysis device. In yet another embodiment, the electrical contact point may be made at the top plate (ITO slide) with a suitable contact means such as a soldered wire or an alligator clip. This contact is connected to the MS power supply for applying a voltage between the microfluidic channel outlet and the inlet to the mass spectrometer.

While the present embodiment illustrates the interfacing of a digital microfluidic array with a microfluidic channel located beneath the digital microfluidic array, it is to be understood that the digital microfluidic array may be interfaced with the microfluidic channel in a variety of different geometries. For example, the digital microfluidic array may be interfaced with a microfluidic channel having an inlet that is laterally adjacent to an element of the digital microfluidic array, as disclosed in PCT Application No. PCT/CA2009/001439, filed Oct. 13, 2009 and titled "Hybrid Digital and Channel Microfluidic Devices and Methods of Use Thereof", Publication No. WO/2010/040227 which is incorporated herein by reference in its entirety.

The methods provided herein are generally automated and are thus typically faster and less prone to operator error when compared to the conventional techniques in terms of sample preparation and reagent use. Specifically, the methods disclosed herein avoid the need to manually process samples dried on filter paper, namely centrifuging the filter paper in an extraction solvent, which involves laborious and time consuming steps.

The aforementioned embodiments may be applied for a wide range of sample types, analytes, and processing applications. Although embodiments disclosed above have focused on three specific metabolic diseases (homocystinuria, phenylketonuria, and tyrosinemia), it is to be understood that the scope of the various embodiments includes, but is not limited to a wide range of analytes that are compatible with digital microfluidic array based extraction and processing.

Example assays include, but are not limited to, amino acid assays, fatty acid disorders (acylcarnitines), organic acid disorders, and markers for metabolic disorders. Tables 1, 2 and 3 below provide a non-limiting list of various known amino acid disorders, fatty acid disorders, and organic acid disorders, respectively, and their markers. The analytes below merely provide an illustrative list and are not intended to limit the scope of the embodiments provided in the present disclosure.

TABLE 1

List of Amino Acid Metabolic Disorders and their Markers

| Amino Acid Disorders | Marker(s) |
|---|---|
| Argininemia or Arginase deficiency | Arginine |
| Citrullinemia-I or Argininosuccinate synthase deficiency | Citrulline |
| Argininosuccinic aciduria or Argininosuccinate lyase deficiency | Citrulline, argininosuccinic acid |
| Ornithine transcarbamylase deficiency | Alanine, Citrulline |
| Carbamoylphosphate synthetase deficiency | Alanine, Citrulline |
| Citrullinemia-II or Citrin-mitochondrial aspartate-glutamate transporterdeficiency | Citrulline |
| Hyperammonemia-Hyperornithine mia-Homocitrullinuria Syndrome | Ornithine |
| Phenylketonuria or Phenylalanine hydroxylase deficiency | Phenylalanine |
| Maple Syrup Urine Disease or Branched chain ketoacid dehydrogenase deficiency | Leucine, Valine |
| Homocystinuria or Cystathioninebeta-synthase deficiency | Methionine |
| Non ketotic hyperglycinemia | Glycine |
| Tyrosinemia I or Fumarylacetoacetase deficiency | Tyrosine |
| Tyrosinemia II or Tyrosine aminotransferase deficiency | Tyrosine |
| Tyrosinemia III or 4-hydroxyphenylpyruvic acid dioxygenase deficiency | Tyrosine |
| 5-Oxoprolinuria or Glutathione synthetase deficiency | 5-oxoproline |
| Biopterin defects | Phenylalanine |

TABLE 2

List of Fatty Acid Metabolic Disorders and their Markers

| Fatty Acid Oxidation Disorders | Marker(s) |
|---|---|
| Very long-chain acyl-CoA dehydrogenase deficiency | Tetradecenenoylcarnitine, Tetradecanoylcarnitine |
| Long-chain hydroxyacyl-CoA dehydrogenase deficiency | Hydroxyhexadecanoylcarnitine, Octadecenenoylcarnitine, Hydroxyoctadecenenoylcarnitine |
| Medium-chain acyl-CoA dehydrogenase deficiency | Octanoylcarnitine, Hexanoylcarnitine, Decanoylcarnitine |
| Short-chain acyl-CoA dehydrogenase deficiency | Butyrylcarnitine & Isobutyrylcarnitine |
| Tri-functional protein deficiency | Hydroxyhexadecanoylcarnitine, Hydroxyoctadecenenoylcarnitine, Hydroxyoctadecanoylcarnitine |
| Glutaric aciduria-II or Multiple acyl-CoA dehydrogenase deficiency | Butyrylcarnitine & Isobutyrylcarnitine, Isovalerylcarnitine & 2-methylbutyrylcarnitine, Glutarylcarnitine, Octanoylcarnitine, Tetradecanoylcarnitine |
| Carnitine palmitoyl transferase deficiency-I | Free carnitine |
| Carnitine palmitoyl transferase deficiency-II | Octadecenenoylcarnitine, Hexadecanoylcarnitine |
| Carnitine/acylcarnitine translocase deficiency | Octadecenenoylcarnitine, Hexadecanoylcarnitine |
| Carnitine uptake defect or 2,4-Dienoyl-CoA reductase deficiency | Free carnitine, Decadienoylcarnitine |
| Hydroxyacyl-CoA dehydrogenase deficiency or Short/Medium-chain hydroxyacyl-CoA dehydrogenase deficiency | Hydroxybutyrylcarnitine |
| Propionic acidemia or Propionyl-CoA carboxylase deficiency | Propionylcarnitine |

TABLE 3

List of Organic Acid Metabolic Disorders and their Markers

| Organic Acid Disorders | Marker(s) |
|---|---|
| Methylmalonic aciduria or Methylmalonyl-CoA mutase deficiency | Propionylcarnitine |
| Cobalamin defects (A, B) | Propionylcarnitine |
| Cobalamin defects (C, D) | Propionylcarnitine, Methionine |
| Multiple carboxylase deficiency | Propionylcarnitine, Hydroxyisovalerylcarnitine |
| 3-Hydroxyisobutyric aciduria | Hydroxybutyrylcarnitine |
| Isovaleric acidemia or Isovaleryl-CoA dehydrogenase deficiency | Isovalerylcarnitine & 2-methylbutyrylcarnitine |
| 2-Methylbutyrylglycinuria or 2-Methylbutyryl-CoA dehydrogenase deficiency | Isovalerylcarnitine & 2-methylbutyrylcarnitine |
| 3-Methylcrotonyl-CoA carboxylase deficiency | Hydroxyisovalerylcarnitine |
| 3-Hydroxy-3-methylglutaryl-CoA lyase deficiency | Hydroxyisovalerylcarnitine, |
| Mitochondrial acetoacetyl-CoA thiolase deficiency or Beta-ketothiolase deficiency | Tiglylcarnitine plus 3-methylcrotonylcarnitine |
| Methylglutaconic aciduria or 3-Methylglutaconyl-CoA hydratase deficiency | Tiglylcarnitine plus 3-methylcrotonylcarnitine |
| 2-Methyl-3-hydroxybutyryl-CoA dehydrogenase deficiency | Hydroxyisovalerylcarnitine |
| Malonic aciduria or Malonyl-CoA decarboxylase deficiency | Malonylcarnitine |
| Glutaric aciduria-I or Glutaryl-CoA dehydrogenase deficiency | Glutarylcarnitine |

It is to be understood that while the preceding embodiments have included a derivatization step for processing the extracted analyte using the digital microfluidic array, this step may not be required for extraction protocols that are suitable for other analytes. As such, the derivatization step, or any further on-chip processing steps, may be optionally performed, as appropriate for a given analyte or application.

Example applications include, but are not limited to, neonatal screening of metabolic disorders (i.e. amino acids and organic acids), other disorders (for example, congenital adrenal hyperplasia, congenital hypothyroidism, biotinidase deficiency and galactosemia), and genetic disorders (e.g. cystic fibrosis and sickle cell diseases).

For example, in each newborn blood spot analysis, a sample is obtained by pricking the subject's heel (or by venipuncture) and allowing a spot of blood to dry on filter paper. The dried blood spot is typically couriered to a lab, where 3.2 mm diameter circular discs are punched, and the analytes are extracted, mixed with isotope-labeled internal standards, derivatized, and then reconstituted for analysis by tandem mass spectrometry (MS/MS). As shown in FIG. 3(a), the derivatization step transforms each amino acid to its corresponding butyl ester (derivatized amino acid) that allows for a characteristic fragmentation pattern (neutral loss of 102) via collision induced dissociation. FIGS. 3(b-c) contains representative primary (MS1) and secondary (MS2) mass spectra for the amino acid, phenylalanine, with peaks at m/z 222 and 120. In addition to amino acids, the same derivatization step butylates acylcarnitines (AC), which serve as markers of inborn errors of fatty acid and organic acid metabolism.

An additional and clinically relevant advantage of the present digital microfluidic methods is the reduction in sample size that may be achieved relative to conventional processing methods. In some cases, the reduction in volume may be approximately 15-20×. This reduction has the potential to be beneficial for applications in which it is desirable to employ small sample volumes, such as in the testing of newborn patients, from which five spots of blood are typically collected for analysis, and in high throughput screening applications.

In the examples provided herein, the small volume required (5×5 µL=25 µL) for certain clinical in-vitro diagnostic assays can be collected as capillary blood with a single needle-prick, but in conventional sample processing methods, the volume (5×75-100 µL=375-500 µL) often requires multiple pricks and tissue-squeezing, which can contaminate the sample with interstitial fluids, invalidating it for testing. Other sample size-related advantages of the present embodiments are a reduction in reagent use (fpr example, 20 µL vs. 170-450 µL), and a reduction in analysis time (~1 h vs. >3.5 h). This reduction in reagents and analysis time, combined with the potential elimination of sample preparation robotic liquid handling systems, makes the present methods an attractive option for diagnostic testing in a time of increasing costs for health care.

The following examples are presented to enable those skilled in the art to understand and to practice the present invention. They should not be considered as a limitation on the scope of the invention, but merely as being illustrative and representative thereof.

Example 1

Device Fabrication and On-Chip Processing of Amino Acids

Digital microfluidic devices were fabricated in the University of Toronto Emerging Communications Technology Institute (ECTI) cleanroom facility, using a transparent photomask printed at Norwood Graphics (Toronto, ON). Glass devices bearing patterned chromium electrodes were formed by photolithography and etching and were coated with 2.5 µm of Parylene-C and 50 nm of TEFLON-AF. Parylene-C was applied using a vapor deposition instrument (Specialty Coating Systems), and Teflon-AF was spin-coated (1% wt/wt in Fluorinert FC-40, 2000 rpm, 60 s) followed by post-baking on a hot-plate (160° C., 10 min). The polymer coatings were removed from contact pads by gentle scraping with a scalpel to facilitate electrical contact for droplet actuation.

A prototype similar to the device shown in FIG. 1 was fabricated to analyze 5-µL blood samples. As shown in the top image, an array of 88 driving electrodes connects a series of 10 reservoirs dedicated to microliter volumes of sample and reagents. As depicted in the bottom image, blood samples are spotted onto the device and dried, after which the sample is extracted into methanol and the solvent is allowed to evaporate. The extract is then derivatized, and the product is isolated by allowing the solvent to evaporate. The entire process requires 50 min to complete (compared with >3.5 h for clinical laboratories, not including mailing time).

The device featured an array of eighty-eight actuation electrodes (2.2×2.2 mm ea.) connected to ten reservoir electrodes (5×5 mm ea.), with inter-electrode gaps of 40 µm. Devices were assembled with an unpatterned ITO-glass top plate and a patterned bottom plate separated by a spacer formed from four pieces of double-sided tape (total spacer thickness 360 µm). Unit droplets (covering a single driving electrode) were ~1.8 µL. To actuate droplets, driving potentials (70-100 $V_{RMS}$) were generated by amplifying the output of a function generator (Agilent Technologies, Santa Clara, Calif.) operating at 18 kHz. As described elsewhere, droplets were sandwiched between the two plates and actuated by applying driving potentials between the top electrode (ground) and sequential electrodes on the bottom plate via the exposed contact pads. Droplet actuation was monitored and recorded by a CCD camera mounted on a lens.

Blood samples were collected from a healthy adult male volunteer after a 10 h fasting period and were kept at −20° C. until analysis. Immediately prior to use, samples were thawed and evaluated as described.

Working solutions of all amino acids (amino acids) (25, 50, 100 and 500 µM ea.) were prepared in DI water. For derivatization of extracted amino acids, a 3 N HCl-butanol solution was prepared from a mixture of 12 N HCl/neat butanol (1:3 v/v). For analysis of amino acids in blood samples, the extracting solvent (MeOH) contained 25 µM of the appropriate deuterated amino acid ($d_3$-Met, $d_5$-Phe or $d_4$-Tyr). For quantitative analysis of amino acid recovery from blood and for experiments mimicking diseased/healthy infant blood, samples were spiked with 200 µM of the appropriate amino acid (Met, Phe or Tyr). In all experiments, organic solvents were HPLC grade and deionized (DI) water had a resistivity of 18 MΩ·cm at 25° C.

5-µL droplets containing the sample (i.e., amino acid standards, whole blood or spiked whole blood) were pipetted onto the bottom plate of a device and dried. The top plate was then affixed and two solvents were loaded into the appropriate reservoirs, including MeOH containing 25 µM of deuterated amino acid (extraction solvent), and 3 N HCl-butanol (derivatization solvent). A reservoir volume (10 µL) of extraction solvent was dispensed and driven by digital microfluidic to the dried sample and allowed to incubate (5 min). The extraction solvent was then actuated away from the sample and dried (~15 min, room temperature) at a second site, after which a reservoir volume (10 µL) of derivatization solvent was dispensed to the dried extract and incubated for 15 min at 75° C. Following the reaction, the top plate was removed and the solvent was allowed to evaporate (~15 min, room temperature).

Figure 5:
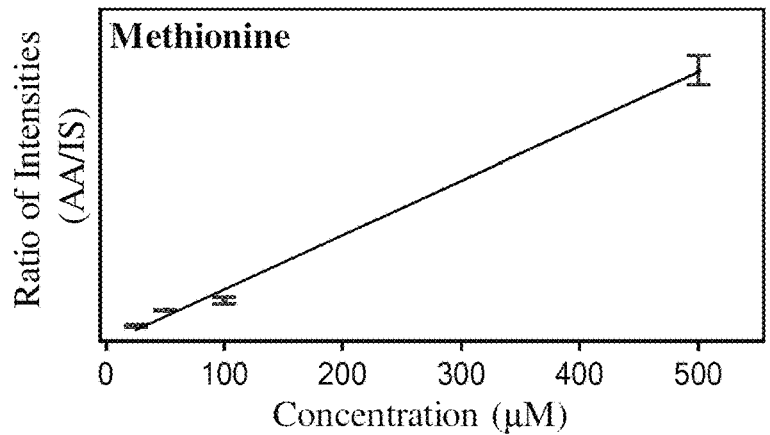
FIG. 5 provides calibration curves generated by digital microfluidic sample preparation for quantification of three amino acids in blood.
Figure 5:
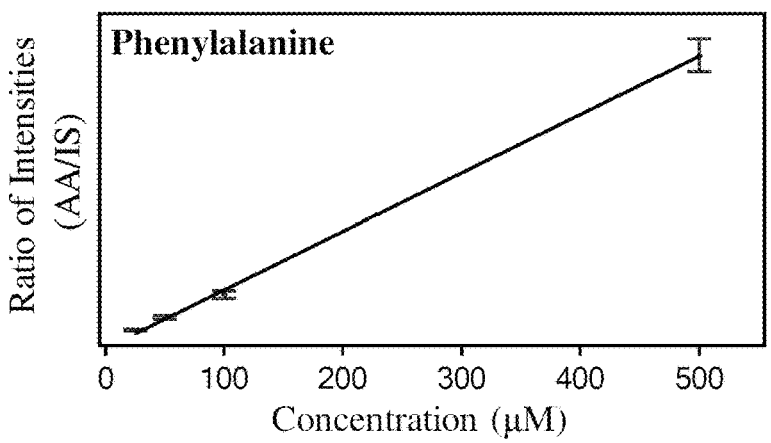
Figure 5:
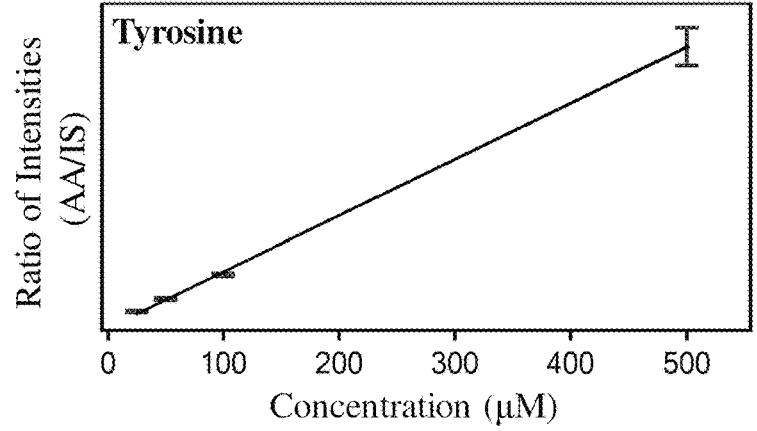

Calibration curves were generated by digital microfluidic sample preparation for quantification of (a) methionine (Met), (b) phenylalanine (Phe), and (c) tyrosine (Tyr) in blood. As shown in FIG. 5, data was generated by plotting the intensity ratios of the daughter ions of each amino acid relative to their deuterated internal standard (i.e., d3-Met, d5-Phe, d4-Tyr, respectively) as a function of amino acid concentration. Each data point represents at least four replicate measurements, and error bars represent ±1 S.D. Regression lines were linear with $R^2$>0.996 for each analyte.

For comparison, amino acids were also extracted and derivatized on the macroscale using known methods. Amino acid samples (20 µL) were pipetted and dried in a microcentrifuge tube and extracted in methanol (500 µL, 30 min) containing isotope-labeled internal standards. The solution was centrifuged (13,000 rpm, 15 min), and the supernatant transferred to a second tube and evaporated to dryness using nitrogen. The extractate was then resuspended in 3 N HCl-butanol solution (250 µL) to derivative the amino acids at 65° C. for 20 min, followed by evaporation of the derivatized mixture.

Most samples were processed by digital microfluidic and then were analyzed offline by nanoelectrospray tandem mass spectrometry (nESI-MS/MS). Such samples (stored dry on device or in centrifuge tube until analysis) were reconstituted in 70 µl of acetonitrile/water (4:1 v/v); samples originating from blood were, in addition, passed through PVDF membrane centrifuge-filters with 0.1 µm pore diameter (Millipore, ON). Samples were injected into an LTQ Mass Spectrometer (Thermo Scientific) via a fused silica capillary transfer line (100 µm i.d.) mated to a New Objective Inc. (Woburn, Mass.) nanoelectrospray emitter (100 µm i.d. tapering to 50 µm i.d.) at a flow rate of 0.8 µL min, with an applied voltage of 1.7-1.9 kV and capillary temperature of 200° C. Tandem MS/MS analysis was carried out by introducing 30% collision energy to the parent ions and then the fragments over the m/z range of 100-300 were scanned. For amino acid samples, the daughter ions detected in the second mass selection, which exhibit a loss of butylformate ($HCOOC_4H_9$, 102 m/z), were observed and used for quantification. Spectra were collected as an average of 50 acquisitions, and replicate spectra were obtained for digital microfluidic-derivatized samples of both control and blood.

Some samples were analyzed by nESI-MS/MS in-line on hybrid digital microfluidic-microchannel devices bearing an integrated nESI emitter. In these experiments, hybrid devices were mounted on a 3-axis micromanipulator (Edmund Optics, N.J.) positioned near the inlet of the LTQ MS. After sample processing, a spray was generated by applying 2.5-3.0 kV to a platinum wire inserted in the access hole (see FIG. 6).

Tandem mass spectrometry was used to (i) quantify amino acids in blood samples and (ii) evaluate the recovery efficiency of the digital microfluidic method. For the former (quantification of amino acid in blood samples), calibration plots were generated by plotting the intensity ratio of daughter ions from the extracted amino acids relative to the those of the internal standards (i.e., Met m/z 104:107, Phe m/z 120:125, and Tyr m/z 136:140) as a function of amino acid concentration in standard solutions (25-500 µM in DI water). Data points included in the calibration plots represent an average of at least 4 replicate measurements, and the data in each plot were fit with a linear regression. Blood samples were then evaluated (with on-chip derivatization and extraction, and measurement by MS/MS relative to internal standards, as above), and the values were compared to the calibration plots to determine the amino acid concentrations. For the latter (evaluation of % recovery), blood samples of known amino acid concentrations were spiked with 200 µM of amino acid standards and extracted (as above). Knowing the total concentration of amino acids in blood spots (e.g. native methionine concentration plus spiked methionine), % recovery was obtained by comparing the concentration values (obtained from calibration curves) vs. the known values.

The % recovery of amino acids was evaluated quantitatively using a fluorescence-based assay. Control samples (Met, Phe or Tyr; 50 µM of each) were processed by digital microfluidic (as above), excluding the derivatization step. The dried extracts were diluted into 95 µL aliquots of borate buffer (20 mM, pH 8.5) in wells in a 96-well microplate. Upon addition of 5 µL of fluorescamine (5 mg/mL in acetone) the microplate was inserted into a fluorescence microplate reader (Pherastar, BMG Labtech, Durham, N.C.) equipped with a module for 390 nm excitation and 510 nm emission. The plate was shaken (5 s) and the fluorescence was measured. As a control, identical samples that had not been extracted were evaluated using the same fluorescent assay. To ensure that controls were processed in identical manner relative to extracted samples, each control sample was spotted on a device, dried and then reconstituted in buffer for analyses. Four replicate measurements were made for each sample and control.

Nanoelectrospray ionization tandem mass spectrometry (nESI-MS/MS) is used to quantify amino acids in samples of blood processed by the digital microfluidic method. Calibration curves with $R^2$ greater than 0.996 (FIG. 4) were generated by analyzing standards processed by digital microfluidic at known concentrations from the abundance ratio of each amino acid to its deuterated standard peak in the secondary (MS2) spectra. The calibration curves facilitated measurement of amino acid concentrations in blood samples from a healthy male volunteer. As listed in Table 4, the values obtained were in the expected physiological range and the precision in the method was high with coefficients of variation (CVs) ranging from 5 to 11%.

TABLE 4

Measured (±1 S.D.) and normal adult concentrations of amino acids in blood.

| Amino Acid | Measured Blood Concentration (µM) in an Adult Male Volunteer | Normal Blood Concentration (µM) |
| --- | --- | --- |
| Methionine | 25 ± 2 | 16-33 |
| Phenylalanine | 38 ± 2 | 41-68 |
| Tyrosine | 46 ± 5 | 45-74 |

Fluorescence and MS/MS were used as an orthogonal test to evaluate the extraction efficiency of the new digital microfluidic technique. The former method relies on fluorescamine, a fluorogenic reagent that exhibits no fluorescence until it reacts with primary amines. Recovery was determined by comparing the fluorescence intensity of multiple samples before and after extraction. In the latter (MS/MS) method, blood samples were spiked with amino acid and recovery was determined by comparing the amino acid concentration (native amino acid plus spiked amino acid) vs. known concentration. As listed in Table 5, the two orthogonal methods (fluorescence and MS/MS) agree and reveal the new technique to be very efficient and recovery was ≥80% for each standard and blood sample evaluated. As above, the precision of these measurements was high, with CVs ranging from 1 to 10%.

TABLE 5

% Recovery of the digital microfluidic method measured by fluorescence and MS/MS (±1 S.D.)

| Amino Acid | % Recovery by Fluorescence in Standards | % Recovery by MS/MS in Blood |
| --- | --- | --- |
| Methionine | 98 ± 10 | 100 ± 1 |
| Phenylalanine | 86 ± 9 | 85 ± 5 |
| Tyrosine | 82 ± 10 | 84 ± 7 |

Figure 6:
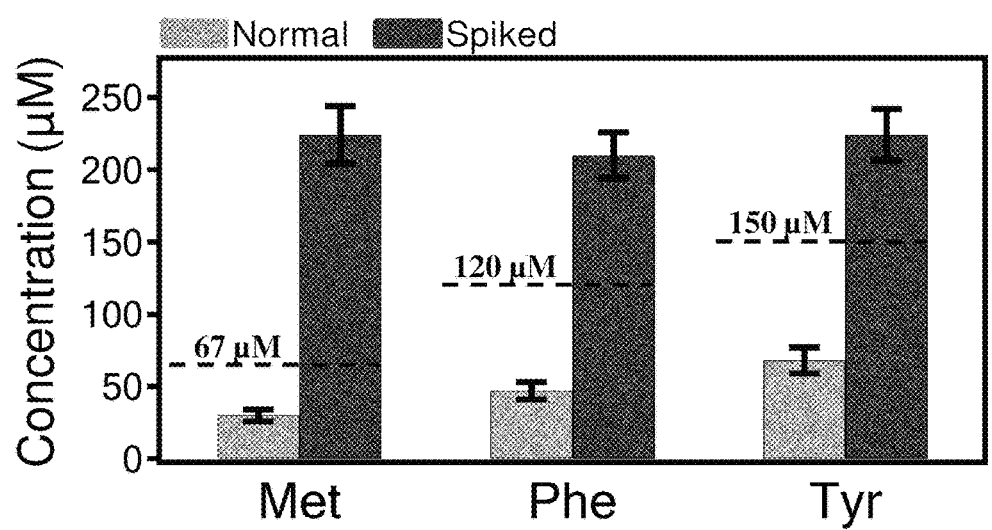
FIG. 6 provides a comparison of Met, Phe, and Tyr concentrations in normal (green) and spiked (red) blood samples as biomarkers for homocystinuria, phenylketonuria, and tyrosinemia, respectively. The dashed lines indicate the upper levels for normal concentrations in newborn blood samples. Each data point represents at least four replicate measurements, and error bars represent ±1 S.D.

To validate the new digital microfluidic method as a platform for analyzing amino acid disorders in blood, spiked blood samples (mimicking diseased states) and non-spiked blood samples (mimicking healthy state) were analyzed by mass spectrometry. FIG. 6 shows a comparison of measured concentration of amino acids in normal and spiked blood samples. The dashed line indicates the threshold value for diagnosis of homocysteinuria (67 µM Met), phenylketonuria (120 µM Phe), and tyrosinemia (150 µM Tyr). As shown, the method is useful for distinguishing between these states.

As shown in FIG. 4, a hybrid digital microfluidic system was fabricated (using process similar to those disclosed above) in which an nESI device was directly integrated with the microfluidic device. The hybrid digital microfluidic-microchannel devices were fabricated in four steps.

First, a DMF bottom substrate (layer 205 in FIG. 4(a)) bearing an array of DMF driving electrodes) was fabricated as described above, but without a TEFLON-AF™ coating).

The design was similar to that of the DMF-only devices described above, but with fewer electrodes—2 rows of 9 actuation electrodes 215 (2.2×x2.2 mm) and 3 reservoir electrodes 220 (5×x5 mm). Moreover, the substrates were first modified by drilling an access hole 230 (~2 mm diameter) through the substrate using a micro drill-press before the photolithographic processes, where the hole was drilled adjacent to the planned location of an electrode 235. After patterning the electrodes, the opposite side was first coated with 7 μm of Parylene-C for bonding with substrate 210.

Secondly, a glass substrate 210 bearing a microchannel 245 nanoelectrospray tip 240 formed in Parylene was fabricated. 37 grams of Parylene-C were deposited on piranha cleaned, silanized glass slide (25=55 mm) via vapor deposition. After Cr deposition, a microchannel (25 μm wide=5 mm long) was photolithographically patterned on the substrate by UV radiation (365 nm, 35 mW/cm2, 50 s) using a Karl-Suss MA6 mask aligner (Garching, Germany).

Third, the channel side of substrate 210 was mated to the non-electrode side of substrate 205, placed under pressure in a precision vise (~20 MPa), and thermally bonded in a vacuum oven (200° C., 24 h). After cooling, the top of substrate 205 was first coated with 2 μm of parylene followed by spin-coating 50 nm of TEFLON-AF with a small piece of dicing tape covering the drilled hole. The tape was removed before post-baking on a hot plate (160° C., 10 min).

Fourth, the top plate 200 was assembled with spacers formed from four pieces of double-sided tape as described above for droplet actuation.

Figure 7:
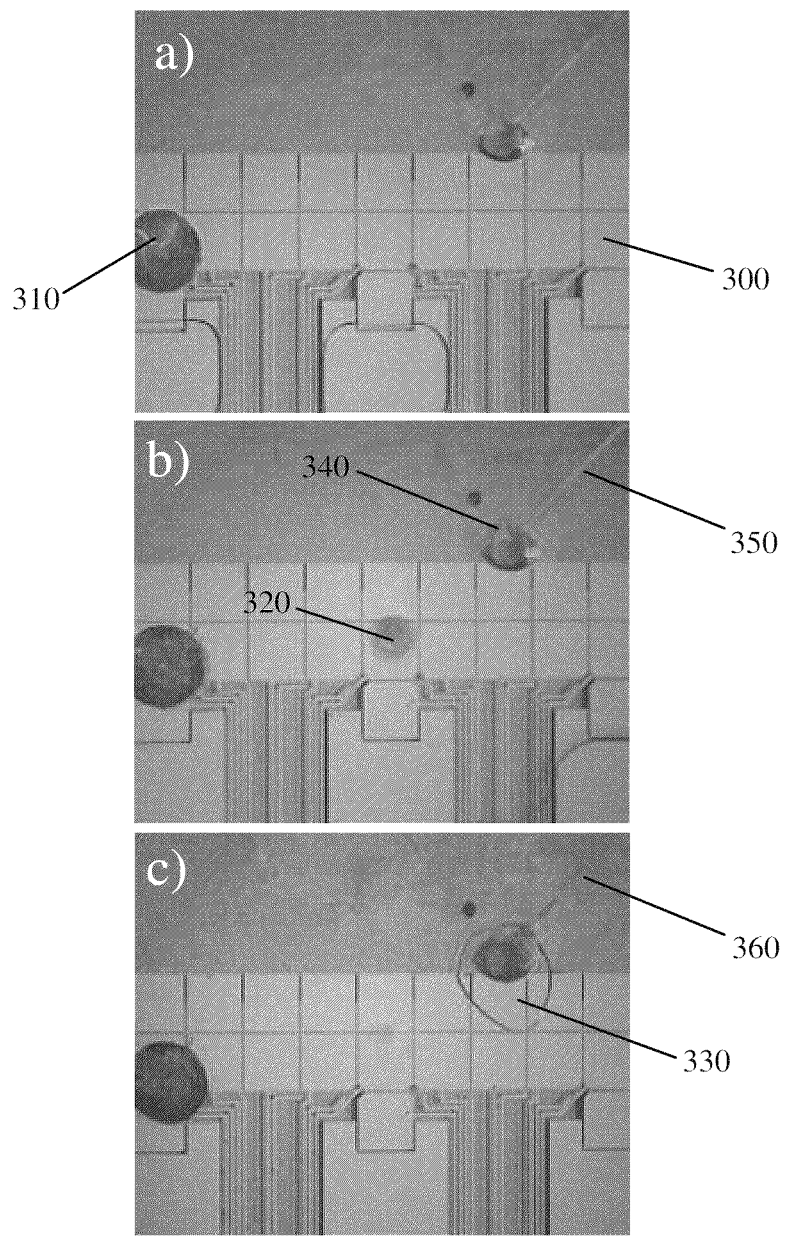
FIGS. 7 (a)-(c) shows a series of frames from a movie (top-to-bottom) demonstrating derivatization and extraction of amino acids, resolubilization in solvent, and analyte solution on a hybrid microfluidic device.

Using this hybrid device, droplets are manipulated on the top surface, and are subsequently transferred to microchannels on the bottom of the device through the hole. The principle of operating the hybrid device for on-chip sample analysis is shown in FIG. 7, which shows several frames from a movie demonstrating derivatization and extraction of amino acids, resolubilization in solvent, and analyte solution on a hybrid microfluidic device. A blood sample 310 was first spotted on the device 300 and the amino acids were extracted and derivatized as described above. The dried, derivatized sample 320 was then resuspended in acetonitrile and the droplet 330 was actuated towards the access hole 340 such that it filled the underlying channel 350. The filled channel can be seen at 360 in FIG. 7(c).

Figure 8:
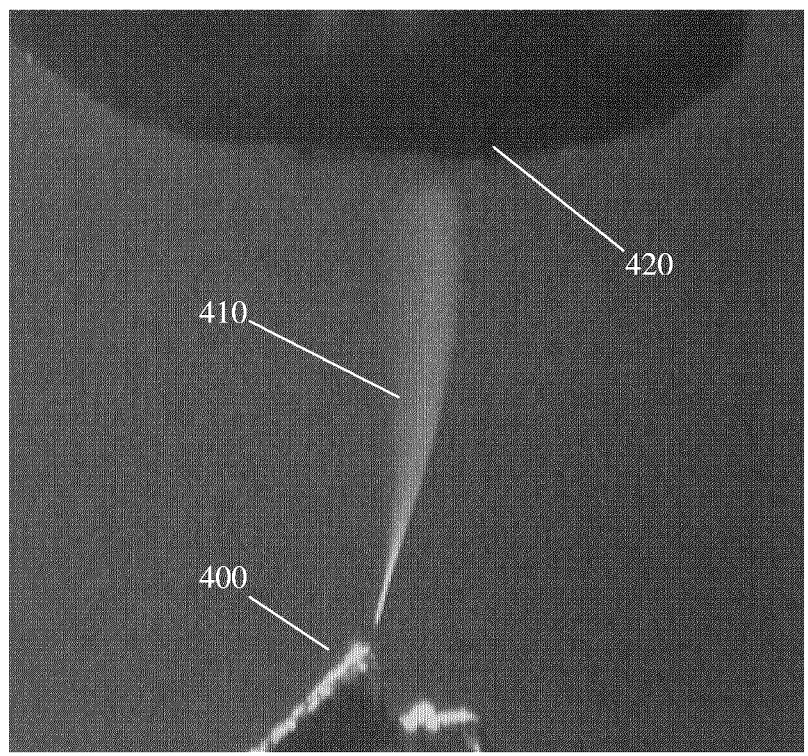
FIG. 8 is an image of sample spraying from the fabricated emitter into a mass spectrometer inlet.
Figure 9:
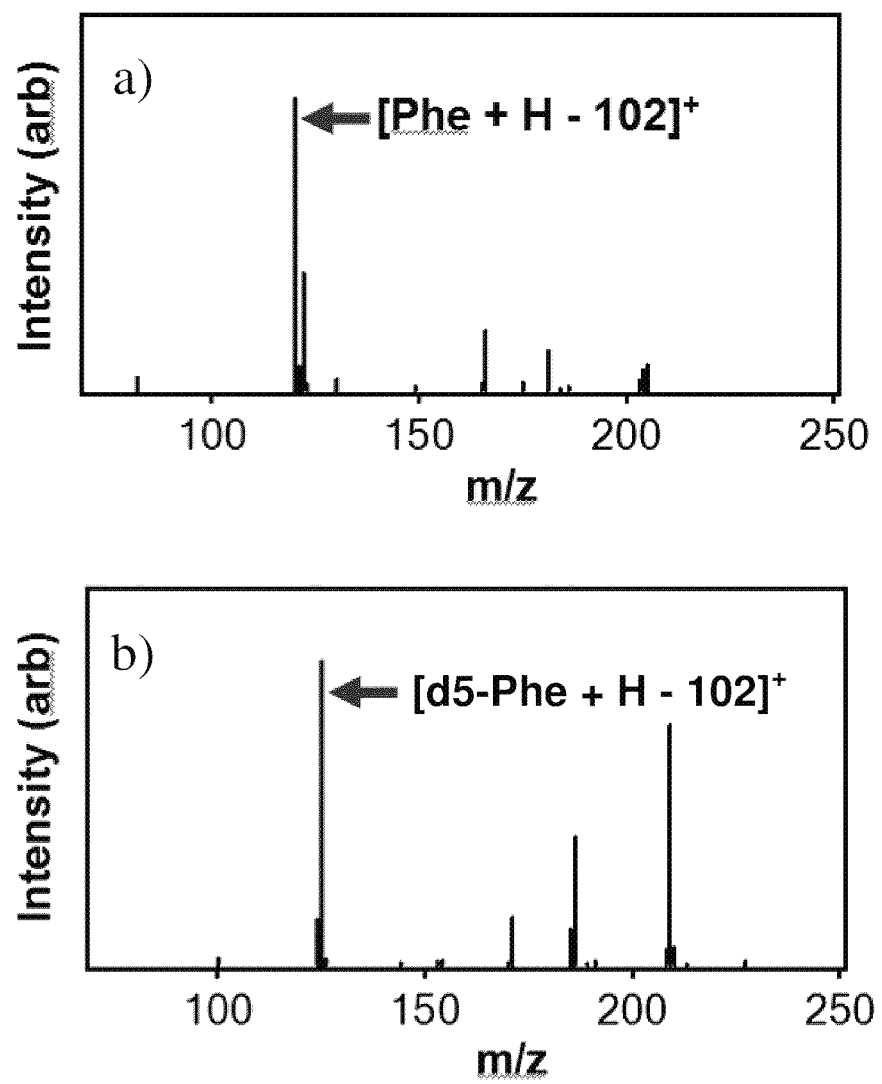
FIG. 9 plots the secondary analysis spectra of (a) Phe and (b) d5-Phe generated from blood samples.

As shown in FIG. 8, the fluid in the channel was delivered to a corner 400 of the device and nanoelectrospray 410 was generated by applying a high voltage to the counter electrode 420. Representative mass spectra generated from samples processed and analyzed on-chip are shown in FIG. 9. The entire process requires ~1 h from sampling to analysis, and requires only the hybrid digital microfluidic device and a mass spectrometer (i.e., no complex nanoflow pumps, robots, samplers, or control software).

Example 2

Direct Digital Microfluidic Processing of Sample Dried on Solid Phase

In the present example, a digital microfluidic method is demonstrated using the direct processing, on a digital microfluidic array, of samples dried onto filter paper. A digital microfluidic array device was fabricated as described in Example 1, except that in the present case, the two plates were separated by six pieces of double-sided tape (total spacer thickness 540 μm). This increased spacing was provided to accommodate the thickness of the filter paper. A blood sample was collected and dried onto filter paper, and a 3.2 mm diameter filter paper disc was punched for subsequent analysis. The punch was placed onto an element of a digital microfluidic array.

A portion of an experiment is depicted in FIG. 10(a). As shown, a droplet of extraction solvent 510 was dispensed on the digital microfluidic array 500 and driven to the filter paper punch 520, and the extract was then moved away and dried 530 for further processing (i.e., derivatization and solvent exchange, similar to FIG. 1). As can be seen in FIG. 10(b), after wetting, the filter paper punch 520 remains adhered to the surface through capillary forces. This process requires ~50 min to complete.

To evaluate this digital microfluidic method relative to gold standard practices, a series of punches from blood samples containing various concentrations of Phe were processed by this digital microfluidic method, and punches from the same samples were evaluated using the conventional newborn screening technique. As listed in Table 6 below, a paired t-test revealed no significant difference between the two data sets at a 95% confidence level. To validate the new technique for application to clinical samples, dried blood spot punches from three newborn patients of NSO were evaluated by the digital microfluidic method. As shown in FIG. 10(b), the new technique correctly identified patients 1 and 3 as suffering from phenylketonuria, and patient 2 as being unaffected.

TABLE 6

Measured phenylalanine (Phe) concentration in 3.2 mm dia. punches from filter paper bearing dried blood using digital microfluidic method 2 (left) and standard techniques at NSO (right). A paired t-test (P = 0.05, t = 0.69) revealed no significant difference between the two data sets.

| Sample | Measured Phe Concentration (μM) Using DMF Method 2 | Measured Phe Concentration (μM) Using NSO Technique |
|---|---|---|
| 1 | 70 | 70 |
| 2 | 550 | 548 |
| 3 | 93 | 88 |
| 4 | 93 | 92 |
| 5 | 368 | 302 |
| 6 | 534 | 539 |
| 7 | 735 | 871 |

The foregoing description of the embodiments of the invention has been presented to illustrate the principles of the invention and not to limit the invention to the particular embodiment illustrated. It is intended that the scope of the invention be defined by all of the embodiments encompassed within the following claims and their equivalents.

What is claimed is:

1. A method of sample preparation in a two-plate digital microfluidic device comprising an array of digital microfluidic elements that can be electrically actuated, the method comprising the steps of:

placing a solid phase support at a first location so that said solid phase support is sandwiched between an upper plate and a lower plate of said two-plate digital microfluidic device, wherein said solid phase support comprises a dried sample, wherein said first location is dropwise addressable under actuation of said two-plate digital microfluidic device, further wherein a lateral extent of said solid phase support is limited to a portion of the array of digital microfluidic elements to permit a transfer of droplets by said array of digital microfluidic elements;

actuating said two-plate digital microfluidic device to transport a droplet of an extraction solvent from a second location that is dropwise addressable under actuation of said two-plate digital microfluidic device to said first location; and incubating said droplet of said extraction solvent to extract an analyte from said dried sample into said droplet of said extraction solvent, wherein said dried sample is selected from the group consisting of: dried whole blood, dried serum, dried plasma, dried urine, dried sputum, and dried cerebral spinal fluid.

2. The method according to claim 1 wherein said solid phase support comprises a porous solid phase.

3. The method according to claim 1 wherein said solid phase support comprises filter paper.

4. The method according to claim 3 further comprising punching said filter paper to a pre-selected size prior to placing said solid phase support at said first location.

5. The method according to claim 1 wherein said solid phase support comprises one of: cellulose, nitrocellulose, and a porous polymer monolith.

6. The method according to claim 1 wherein a lateral extent of said solid phase support is less than one digital microfluidic element of the array of digital microfluidic elements.

7. The method according to claim 1 wherein placing said solid phase support at said first location comprises the steps of:

contacting said solid phase support with said lower plate; and installing said upper plate.

8. The method according to claim 1 wherein placing said solid phase support at said first location comprises inserting said solid phase support between said lower plate and said upper plate.

9. The method according to claim 1 further comprising receiving, from a remote collection location, said solid phase support comprising said dried sample.

10. The method according to claim 1 wherein said droplet of said extraction solvent is a first droplet of said extraction solvent, said method further comprising:

placing an additional solid phase support at a third location between said upper plate and said lower plate of said two-plate digital microfluidic device, wherein said additional solid phase support comprises a second dried sample, wherein said third location is dropwise addressable under actuation of said two-plate digital microfluidic device;

actuating said two-plate digital microfluidic device to transport an additional droplet of said extraction solvent to said third location;

incubating said additional droplet of said extraction solvent to extract a second analyte from said second dried sample into said additional droplet of said extraction solvent; and actuating said two-plate digital microfluidic device to contact said additional droplet of said extraction solvent with said first droplet of said extraction solvent.

11. The method according to claim 1 wherein said extraction solvent comprises a polar solvent.

12. The method according to claim 1 wherein said analyte is selected from the group consisting of an amino acid, fatty acid, acylcarnitine, and organic acid.

13. The method according to claim 1 wherein said analyte is a marker of a metabolic disorder.

14. The method according to claim 1 further comprising:

transporting said droplet of extraction solvent after incubation to extract said analyte to a third location that is addressable by said two-plate digital microfluidic device;

drying said droplet of extraction solvent to form a dried droplet of extraction solvent and extracted analyte;

actuating said two-plate digital microfluidic device to transport a droplet of a derivatization solvent to said third location; and incubating said droplet of said derivatization solvent with said dried droplet of extraction solvent and extracted analyte to obtain a derivatized analyte that is dissolved or suspended in said derivatization solvent.

15. The method according to claim 14 wherein said microfluidic device further comprises a microfluidic channel and an electrical contact for electrically contacting a fluid in said microfluidic channel, wherein an inlet of said microfluidic channel is interfaced with a gap between said upper and lower plate of said two-plate digital microfluidic device such that said two-plate digital microfluidic device may be actuated to contact a droplet with said microfluidic channel and fill said microfluidic channel, and wherein an outlet of said microfluidic channel provides an opening in an external surface of said microfluidic device, said method further comprising the steps of:

electrically addressing said two-plate digital microfluidic device to transport said droplet of derivatization solvent comprising said derivatized analyte and to contact said droplet of derivatization solvent with said inlet of said microfluidic channel to fill said microfluidic channel;

positioning said outlet of said microfluidic channel adjacent to an inlet of a mass analysis device; and generating an electrospray cone, said cone emerging from said microfluidic channel and into said inlet of said mass analysis device, by applying a voltage between said electrical contact and said inlet of said mass analysis device.

16. The method according to claim 15 further comprising the step of performing a mass analysis assay for said analyte.

17. The method according to claim 15 wherein said mass analysis device is a tandem mass spectrometer.

18. The method according to claim 15 wherein said electrical contact is located within an opening in said microfluidic channel.

19. The method according to claim 15 wherein said outlet is located at a corner of said microfluidic device.

20. A method of sample preparation in a two-plate digital microfluidic device comprising an array of digital microfluidic elements that can be electrically actuated, the method comprising the steps of:

placing a solid phase support at a first location so that said solid phase support is sandwiched between an upper plate and a lower plate of said two-plate digital microfluidic device, wherein said solid phase support comprises a dried sample, wherein said first location is dropwise addressable under actuation of said two-plate digital microfluidic device, further wherein a lateral extent of said solid phase support is limited to a portion of the array of digital microfluidic elements to permit a transfer of droplets by said array of digital microfluidic elements, wherein said solid phase support comprises filter paper;

punching said filter paper to a pre-selected size prior to placing said solid phase support at said first location;

actuating said two-plate digital microfluidic device to transport a droplet of an extraction solvent from a second location that is dropwise addressable under actuation of said two-plate digital microfluidic device to said first location; and incubating said droplet of said extraction solvent to extract an analyte from said dried sample into said droplet of said extraction solvent.

\* \* \* \* \*